United States Patent [19]

Moniot et al.

[11] Patent Number: 6,162,913

[45] Date of Patent: Dec. 19, 2000

[54] PREPARATION OF [4S-(4α,7α,10Aβ)]-4-AMINO-OCTAHYDRO-5-OXO-7H-PYRIDO[2,1-B][1,3]THIAZEPINE-7-CARBOXYLIC ACID, METHYL ESTER AND SALTS THEREOF VIA NOVEL DISULFIDES

[75] Inventors: Jerome L. Moniot, Chester; Sushil K. Srivastava, Dayton, both of N.J.; William J. Winter, Montgomery, N.Y.; John J. Venit; Shankar Swaminathan, both of North Brunswick, N.J.; Keith Ramig, Orange, N.J.; Paul A. Jass, Charles City, Iowa; Mark D. Schwinden, Holland, Pa.; John L. Dillon, Jr.; Saibaba Racha, both of East Syracuse, N.Y.; James Simpson, Belle Mead, N.J.; Chien-Kuang Chen, Marlboro, N.J.; Shawn K. Pack, Plainsboro, N.J.

[73] Assignee: Bristol-Myers Squibb Co., Princeton, N.J.

[21] Appl. No.: 09/349,861

[22] Filed: Jul. 8, 1999

Related U.S. Application Data

[60] Provisional application No. 60/092,934, Jul. 15, 1998.

[51] Int. Cl.[7] ............ C07D 281/02; C07C 261/00; C07C 229/04; C07C 229/22
[52] U.S. Cl. ............ 540/490; 540/490; 560/25; 560/169
[58] Field of Search ............ 560/25, 169; 540/490

[56] References Cited

U.S. PATENT DOCUMENTS 5,508,272  4/1996  Robl ............ 514/80

FOREIGN PATENT DOCUMENTS

| WO99/35145 | 7/1999 | WIPO . |
| WO00/03981 | 1/2000 | WIPO . |
| WO00/04179 | 1/2000 | WIPO . |
| WO00/14265 | 3/2000 | WIPO . |

OTHER PUBLICATIONS

Umemoto et al., Bull. chem. Soc. Japan, vol. 59, p. 447–452 (1986).

*Primary Examiner*—Mukund J. Shah
*Assistant Examiner*—Ben Schroeder
*Attorney, Agent, or Firm*—Stephen B. Davis

[57] ABSTRACT

N-protected-L-homocysteine disulfide of the formula

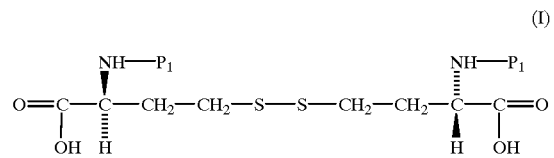

or an activated form thereof is reacted with (S)-2-amino-6,6-dimethoxyhexanoic acid, methyl ester to give the disulfide intermediate of the formula

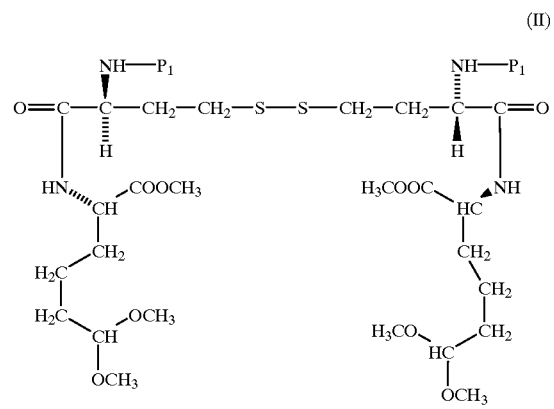

Cleavage of the disulfide bond followed by acid catalyzed cyclization produces the N-protected lactam of formula III which is useful for preparing the pharmaceutically active compound omapatrilat.

28 Claims, No Drawings

PREPARATION OF [4S-(4α,7α,10Aβ)]-4-AMINO-OCTAHYDRO-5-OXO-7H-PYRIDO[2,1-B][1,3]THIAZEPINE-7-CARBOXYLIC ACID, METHYL ESTER AND SALTS THEREOF VIA NOVEL DISULFIDES

This application claims priority from Ser. No. 60/092,934 filed Jul. 15, 1998.

BACKGROUND OF THE INVENTION

Robl in U.S. Pat. No. 5,508,272 disclose compounds of the formula

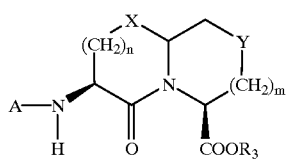

wherein A can be

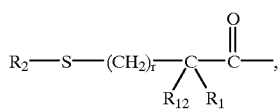

X can be S, Y can be $CH_2$, m can be one, and n can be two as possessing neutral endopeptidase and angiotensin converting enzyme inhibition activity. Among these compounds is [4S-[4α(R*),7α,10aβ]]-octahydro-4-[(2-mercapto-1-oxo-3-phenylpropyl)amino]-5-oxo-7H-pyrido[2,1-b] [1,3]thiazepine-7-carboxylic acid which is currently undergoing clinical evaluation. This compound is reported in the literature as BMS 186,716 and as omapatrilat.

Robl discloses that the amino lactam portion of BMS 186,716, i.e. the intermediate

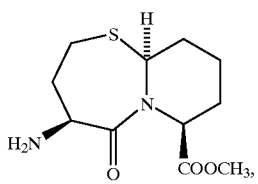

can be prepared by coupling (S)-2-amino-6,6-dimethoxyhexanoic acid, methyl ester with the N-protected amino acid

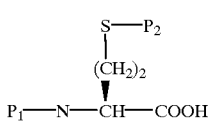

wherein $P_1$ is an amino protecting group and $P_2$ is a sulfur protecting group to give the dipeptide of the formula

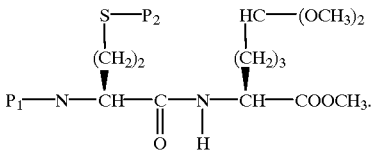

Removal of the $P_2$ protecting group, followed by acid catalyzed cyclization, and removal of the $P_1$ protecting group gives [4S-(4α-(4α,7α,10aβ)]-octahydro-4-amino-5-oxo-7H-pyrido[2,1-b][1,3]thiazepine-7-carboxylic acid, methyl ester.

Robl discloses that $P_1$ is an amino protecting group such as benzyloxycarbonyl, t-butoxycarbonyl, or a group which together with the N-atom forms a protecting group such as phthalimido.

SUMMARY OF THE INVENTION this invention is directed to an improved chemical synthesis of [4S-(4α,7α,10aβ)]-4-amino-octahydro-5-oxo-7H-pyrido[2,1-b] [1,3]thiazepine-7-carboxylic acid, methyl ester as well as salts thereof and novel disulfide intermediates useful in this synthesis.

According to the process of this invention N-protected-L-homocysteine disulfide of the formula

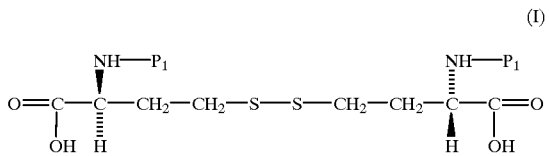

or an activated form of such N-protected-L-homocysteine is reacted with (S)-2-amino-6,6-dimethoxyhexanoic acid, methyl ester to give the disulfide intermediate of the formula

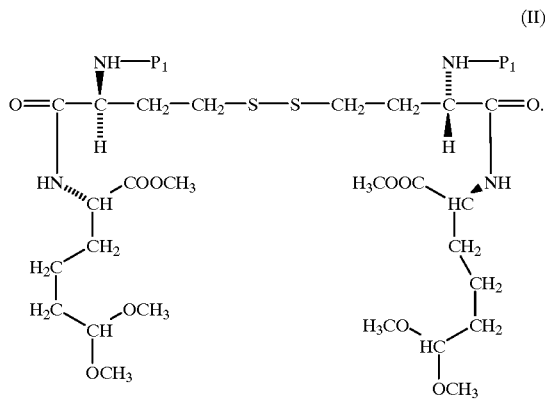

The disulfide intermediate of formula II is then reacted to cleave the sulfur-sulfur bond and the resulting monomer is then cyclized to give the N-protected lactam of the formula

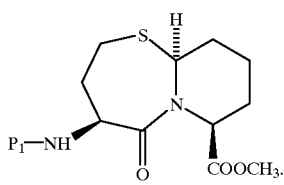

Removal of the $P_1$ protecting group gives the desired lactam [4S-(4α,7α,10aβ)]-4-aminooctahydro-5-oxo-7H-pyrido[2,1-b] [1,3]thiazepine-7-carboxylic acid, methyl ester. This lactam can be converted to a salt such as a hydrohalide salt.

According to another feature of this invention, if the N-protected disulfide of formula I and (S)-2-amino-6,6-dimethoxyhexanoic acid, methyl ester are reacted in an ethyl acetate solution, the ethyl acetate solution of (S)-2-amino-6,6-dimethoxyhexanoic acid is first treated to remove ethylene glycol from the reaction solvent. This results in fewer impurities downstream when the monomer is cyclized to the lactam of formula III. Suitable agents for removing ethylene glycol from the reaction solvent are poly(acrylic acid-co-acrylamide), potassium salt and calcium chloride dihydrate.

DETAILED DESCRIPTION OF THE INVENTION

[4S-(4α,7α,10aβ)]-4-Aminooctahydro-5-oxo-7H-pyrido[2,1-b] [1,3]thiazepine-7-carboxylic acid, methyl ester and salts thereof, particularly a hydrohalide salt thereof, are useful as an intermediate in the preparation of [4S-[4α(R*),7α,10aβ]]-octahydro-4-[(2-mercapto-1-oxo-3-phenylpropyl)amino]-5-oxo-7H-pyrido[2,1-b] [1,3]thiazepine-7-carboxylic acid of the formula

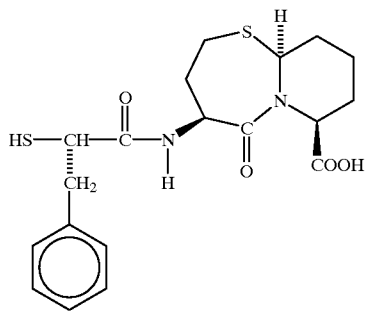

as described by Robl in U.S. Pat. No. 5,508,272.

According to the process of this invention L-homocystine is reacted to introduce the protecting group $P_1$ on both nitrogens giving the disulfide of formula I. Preferred $P_1$ protecting groups include trifluoroacetyl which can be obtained by treating L-homocystine with ethyl trifluoroacetate, phenylmethoxycarbonyl which can be obtained by treating L-homocystine with benzyl chloroformate, and formyl which can be obtained by treating L-homocystine with formic acid and acetic anhydride. Other N-protecting groups such as phthalimido, t-butoxycarbonyl, etc., can be employed according to methods well known in the art. Trifluoroacetyl is the most preferred $P_1$ protecting group.

The N-protected disulfide of formula I is then reacted with (S)-2-amino-6,6-dimethoxyhexanoic acid, methyl ester to give the disulfide intermediate of formula II. This reaction is performed in the presence of a coupling reagent such as dicyclohexylcarbodiimide, 1-ethyl-3-(3-dimethylaminopropyl) carbodiimide, benzotriazol-1-yloxytris(dimethylamino)phosphonium hexafluorophosphate, or carbonyldiimidazole. The preferred coupling reagent is dicyclohexylcarbodiimide. When $P_1$ is trifluoroacetyl, 1-hydroxybenzotriazole is preferably employed along with dicyclohexylcarbodiimide.

If the N-protected disulfide of formula I is reacted with (S)-amino-6,6-dimethoxyhexanoic acid, methyl ester without a coupling reagent, then the salt of the formula

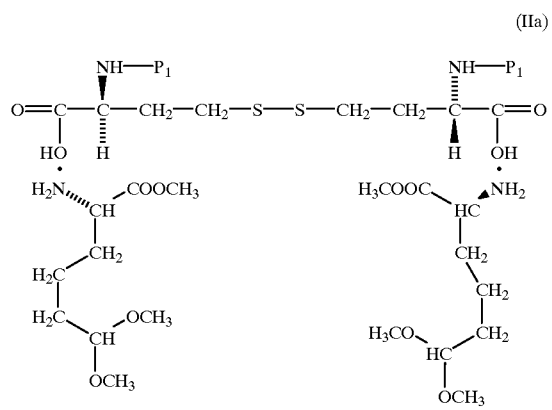

can be formed. Treatment of this salt with a coupling reagent then gives the disulfide intermediate of formula II.

The salt of formula IIa is storage stable meaning that it can be maintained for a period of at least about 30 days under conditions of low temperature and the absence of moisture prior to conversion to the disulfide intermediate of formula II. This affords added flexibility in scheduling production runs and enables different stages of the reaction to be carried out at different manufacturing facilities.

Alternatively, the N-protected disulfide of formula I can be converted to an activated form prior to the reaction with (S)-2-amino-6,6-dimethoxyhexanoic acid, methyl ester. Such activated forms include the acid chloride, mixed anhydrides, symmetrical anhydrides, activated ester, etc. When the activated form of the N-protected disulfide is employed, a coupling reagent is no longer needed. The selection of the activated form depends upon the N-protecting group of the disulfide of formula I. When the protecting group is trifluoroacetyl, suitable activated forms include the acid chloride, which is preferred, and an activated ester. When the protecting group is phenylmethoxycarbonyl, an activated ester is the suitable activated form.

Robl in U.S. Pat. No. 5,508,272 discloses a method for preparing (S)-2-amino-6,6-dimethoxyhexanoic acid, methyl ester. Other methods for preparing this starting material are disclosed in a copending application of Godfrey et al. filed on the same day as this application. Godfrey et al. disclose that the dioxolane pentanoic acid of the formula

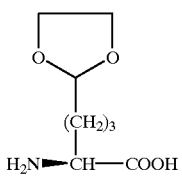

(VII)

can be reacted with thionyl chloride in methanol or with chlorotrimethylsilane and dimethyl sulfite in methanol to give (S)-2-amino-6,6-dimethoxyhexanoic acid, methyl ester.

(S)-2-Amino-6,6-dimethoxyhexanoic acid, methyl ester and the N-protected disulfide of formula I or an activated form thereof are reacted in an organic solvent, preferably n-butyl acetate. If the reaction is performed in ethyl acetate, then, in order to minimize the presence of downstream impurities, the solution of (S)-amino-6,6-dimethoxyhexanoic acid, methyl ester in ethyl acetate is treated to remove ethylene glycol from the reaction solvent prior to reaction with the N-protected disulfide of formula I. Agents suitable for this purpose include poly(acrylic acid-co-acrylamide), potassium salt and calcium chloride dihydrate.

There is an advantage in the process wherein (S)-2-amino-6,6-dimethoxyhexanoic acid, methyl ester is reacted with the acid chloride activated form of the disulfide of formula I in a biphasic solvent system. Under these process conditions, there is no need to first remove ethylene glycol to minimize downstream impurities. Suitable biphasic solvent systems comprise as the organic phase a mixture of ethyl and n-butyl acetate and as the aqueous phase water and a buffering agent such as a mixture of potassium carbonate and potassium bicarbonate.

The N-protected disulfide intermediate of formula II is then reacted to cleave the disulfide bond and the resulting monomer is then cyclized to give the N-protected lactam of formula III. Methods for cleaving the disulfide bond include reacting the intermediate of formula II with a bismercaptan, a phosphine reducing agent, a phosphite reducing agent, or zinc metal powder. Suitable bismercaptans include those of the formula

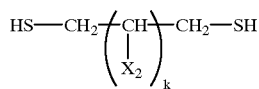

wherein k is an integer from 1 to 4 and each $X_2$ is independently selected from hydrogen and hydroxy as well as 1,2-benzenedimethanethiol, 1,3-butanedithiol meso-α,α'-dimercaptoadipic acid, disodium salt, and durene-α(1),α(2)-dithiol. Preferably, the bismercaptan is reacted in the presence of a base such as sodium methoxide or 1,8-diazabicyclo[5.4.0]undec-7-ene. Preferred bismercaptans are dithiothreitol and dithioerythritol. Suitable phosphine reducing agents include tributyl phosphine, trioctyl phosphine, and triphenyl phosphine. Suitable phosphite reducing agents include triethyl phosphite. The preferred reagent for cleaving the disulfide bond is tributyl phosphine.

The resulting monomer is then subjected to an acid catalyzed cyclization reaction preferably by treating with a strong acid such as trifluoroacetic acid, chlorosulfonic acid, p-toluenesulfonic acid, methanesulfonic acid, trifluoromethanesulfonic acid, trimethylsilyl trifluoromethanesulfonate, trimethylsilyl methanesulfonate or a commercially available polystyrene sulfonate polymer type ion exchange resin such as Amberlyst15®. This cyclization reaction can be performed in a non-protic solvent such as methylene chloride, which is preferred, or chloroform or a protic solvent such as methanol to give the N-protected lactam of formula III.

The N-protected lactam of formula III is then treated to remove the $P_1$ protecting group and give [4S-(4α,7α,10aβ)]-4-aminooctahydro-5-oxo-7H-pyrido[2,1-b] [1,3]thiazepine-7-carboxylic acid, methyl ester. For example, when $P_1$ is trifluoroacetyl treatment with potassium carbonate in methanol can be employed. When $P_1$ is phenylmethoxycarbonyl treatment with iodotrimethylsilane or palladium on carbon and hydrogen can be employed. When $P_1$ is formyl or t-butoxycarbonyl treatment with a strong acid such as hydrochloric acid can be employed.

The lactam [4S-(4α,7α,10aβ)]-4-aminoocta-hydro-5-oxo-7H-pyrido[2,1-b] [1,3]thiazepine-7-carboxylic acid, methyl ester is then reacted with the acylmercaptoalkanoyl sidechain of the formula

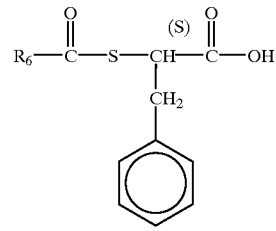

(IV)

wherein $R_6$ is methyl or phenyl giving the compound of the formula

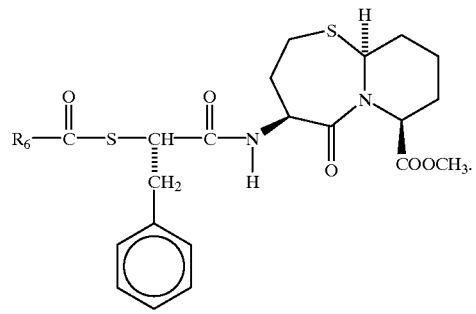

(V)

This coupling reaction can be performed in an organic solvent such as methylene chloride and in the presence of a coupling reagent such as 1-ethyl-3-(3-dimethylaminopropyl)carbodiimide, dicyclohexylcarbodiimide, benzotriazol-1-yloxytris-(dimethylamino)phosphonium hexafluorophosphate, carbonyldiimidazole, or 1-propanephosphonic acid, cyclic anhydride. Alternatively, the acylmercaptoalkanoic acid of formula IV can be converted to an activated form prior to coupling such as an acid chloride, mixed anhydride, symmetrical anhydride, activated ester, etc. Preferably, the lactam is converted to a salt such as a hydrohalide salt before the coupling reaction. Suitable hydrohalide salts include the hydrochloride salt, which is preferred, the hydrobromide, and the hydroiodide. The salt can be prepared by treating a solution of the lactam with the corresponding acid.

The acyl group $R_6$—C(O)— is removed and the methyl ester group is converted to the carboxylic acid from the compound of formula V to give the desired final product of formula VI. For example, when $R_6$ is methyl treatment with sodium hydroxide followed by aqueous acid gives the desired final product of formula VI.

[4S-[4α(R*), 7α,10aβ]]-Octahydro-4-[(2-mercapto-1-oxo-3-phenylpropyl)amino]-5-oxo-7H-pyrido[2,1-b] [1,3]

thiazepine-5-carboxylic acid possesses angiotensin converting enzyme and neutral endopeptidase inhibitory activity. This compound as well as its pharmaceutically acceptable salts are useful in treating cardiovascular diseases such as hypertension and congestive heart failure as note Robl U.S. Pat. No. 5,508,272. This compound can be administered to a mammalian host such as man at from about 0.1 mg to about 100 mg per kg of body weight per day, preferably from about 0.5 mg to about 25 mg per kg of body weight per day. The compound is preferably administered orally but parenteral routes and topical routes can also be employed. The daily dose can be administered singly or can be divided into two to four doses administered throughout the day.

The following examples are illustrative of the invention.

EXAMPLE 1

[4S-(4α,7α,10aβ)]-4-Aminooctahydro-5-oxo-7H-pyrido-[2,1-b] [1,3]thiazepine-7-carboxylic acid, methyl ester, hydrochloride

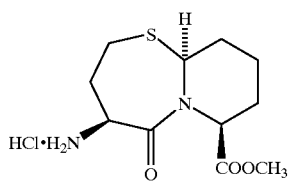

a) N-(Trifluoracetyl)-L-homocysteine, (1→1')-disulfide

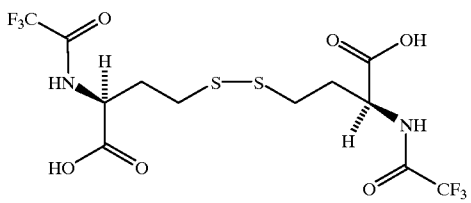

A solution of potassium methoxide in methanol (32 wt %, 68.8 kg) and a methanol rinse (42 kg) were added to solid L-homocystine (40 kg). During the addition, the temperature was maintained at 20±5° C., and a water white solution was produced. Ethyl trifluoroacetate (43.8 kg) was added to this solution and the reaction temperature rose to 35°–40° C., the reaction mixture was treated with 6 wt % hydrochloric acid (432 kg) and ethyl acetate (270 kg). The layers were separated and the organic phase was washed with aqueous acidic brine (168 kg water, 18 kg sodium chloride, 15 kg concentrated hydrochloric acid). the layers were separated and the upper rich organic phase was washed with 20 wt % aqueous brine (183 kg). The layers were separated and the rich ethyl acetate extract was polish filtered and azeotroped at constant volume (110 l) until the moisture level of the fresh distillate showed KF=0.5 (400 kg additional ethyl acetate required. A portion (6 kg) of this rich ethyl acetate was added to warm (65°–70° C.), stirring heptanes and the resultant slurry was vigorously stirred for 30 minutes. The balance of the rich ethyl acetate solution (149 kg) was added over 3.5 hours. After one hour at 65°–70° C., the crystal slurry was cooled to 15°–25° C. over 1.5 hours. After 16 hours at 15°–25° C., the white crystals were isolated and washed (192 kg heptanes, 12 kg ethyl acetate) on a centrifuge filter. Tray drying at 40° C. under reduced pressure afforded 62.3 kg of title product as a white powder; m.p. 123.5° C.

Anal. calc'd for $C_{12}H_{14}F_6N_2O_6S_2$: C, 31.31; H. 3.07; N, 6.09; S, 13.93; F, 24.76. Found: C, 31.28; H, 2.92; N, 5.98; S, 14.28; F, 24,86.

b) (S)-2-Amino-6,6-dimethoxyhexanoic acid, methyl ester

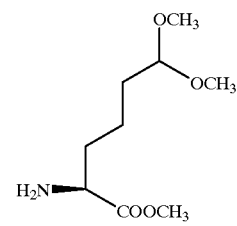

Under nitrogen, chlorotrimethylsilane (28.0 g) was added to a slurry of (S)-α-amino-1,3-dioxolane-2-pentanoic acid (20.9 g) and dimethyl sulfite (12.0 g) in methanol (240 ml) to afford a homogeneous solution. Following the observation of an exotherm to 29° C., the solution was heated to 40–45° C., stirred at that temperature for 8 hours and at about 22° C. for up to 72 hours. In-process HPLC analysis showed that the reaction was complete (about 93 M % conversion to product) and the resulting solution was cooled to −5 to −10° C. With stirring, the apparent pH of the mixture was adjusted to 11.7 to 11.9 by the slow careful addition of 32% (or 4.45 M) methanolic potassium methoxide solution (70 ml) maintaining the temperature in the range of −5 to 0° C. Analysis of the product slurry ($^1$H NMR) indicated that the neutralization was complete. The solvent of the product slurry was exchanged with ethyl acetate by first concentrating the thin slurry under vacuum at less than 30° C. to 300 ml volume followed by the addition of ethyl acetate until the removal of methanol was complete as judged by in-process GC analysis (less than 1 AP). Upon completion of the solvent exchange, the batch volume was adjusted to about 400 ml with ethyl acetate and the resulting slurry was filtered. Poly(acrylic acid-co-acrylamide), potassium salt (3.0 to 3.2 g) and water (30–32 ml) were added to the filtrate. The mixture was stirred for about 35 minutes and filtered. Optionally, the poly (acrylic acid-co-acrylamide), potassium salt treatment can be repeated on the filtrate if the quantity of ethylene glycol exceeds 0.15 equivalents, as judged by in-process GC analysis. Following in-process HPLC analysis, 17.4 g of the title product was obtained as an ethyl acetate solution in 80.8 M % yield.

c) 6,6-Dimethoxy-N-[N-(trifluoroacetyl)-L-homocysteinyl]-L-norleucine, methyl ester, (1→1') disulfide

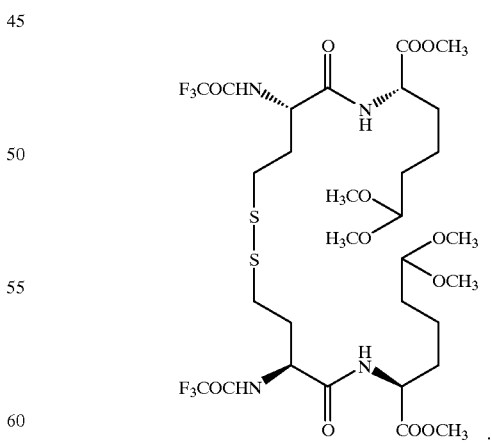

To an ethyl acetate solution of (S)-2-amino-6,6-dimethoxyhexanoic acid, methyl ester (17.4 g, 328 g of solution, 3.5 w % water), N-(trifluoroacetyl)-L-homocysteine, (1→1')-disulfide (19.5 g), hydroxybenzotriazole (0.7 g, 20 w/w % water) and anhydrous sodium sulfate (15 g) were added with stirring. The slurry was cooled to −2 to 2° C. and dicyclohexylcarbodiimide (19 g) was added to the mixture in one portion (slight exotherm). After 5 hours of stirring under a nitrogen atmosphere, in-process HPLC analysis showed that the reaction was complete. The thick dicylcohexylurea and sodium sulfate slurry was filtered and the dicyclohexylurea wet-cake was washed with ethyl acetate (2×10 ml). The combined filtrates were washed with 10% sodium bicarbonate solution (50 ml) and saturated brine solution (50 ml). The rich ethyl acetate layer was concentrated under vacuum keeping the temperature in the range of 35–40° C. to a volume of 130 ml and a water content of less than 0.1 w/w %.

Tert-butyl methyl ether (120 ml) was added to the rich ethyl acetate solution and the resulting hazy solution was polish filtered. The equipment was washed with 1:1 ethyl acetate/tert-butyl methyl ether (2×10 ml) and the wash was combined with the rich filtrate. Cyclohexane (185 ml) was added to the solution at ambient temperature and seed crystals were added. The resulting slurry was agitated for at least 30 minutes and then additional cyclohexane (555 ml) was added over at least 35 minutes. The slurry was agitated for at least one hour and the product wet-cake was washed with 6:1:1 cyclohexane/tert-butyl methyl ether/ethyl acetate solution (75 ml). The wet-cake was dried under vacuum at about 30° C. to give 29.8 g of title product as a white crystalline solid, m.p. 111–112° C.

IR (KBr), 3283 (s), 3087 (w), 2945 (m), 2830 (w), 1743 (s), 1707 (s), 1659 (s), 1546 (m), 1438 (w), 1361 (w), 1211 (s), 1188 (s), 1134 (m) and 1057 (w).

$^1$H-NMR: 300 MHz; $CDCl_3$: δ 1.3–1.5 (m, 2H), 1.5–2.0 (m, 4H), 2.1–2.4 (m, 2H), 2.7–2.9 (m, 2H), 3.3 (s, 6H), 3.8 (s,3H), 4.35 (tr, 1H), 4.6 (m, 1H), 4.9 (m, 1H), 7.5 (d, 1H) and 8.1 (d, 1H). $^{13}$C-NMR: 75 MHz; $CDCl_3$; δ 20.49, 3.36, 31,76, 32.11, 33.89, 52.28, 52.48, 52.56, 52.63, 52.74, 104.0, 115.53 (q), 156.97 (q), 169.29 and 172.48.

d) [4S-(4α,7α,10aβ)]-4-Aminooctahydro-5-oxo-7H-pyrido[2,1-b] [1,3]thiazepine-7-carboxylic acid, methyl ester, hydrochloride To a 1 1 5-necked flask equipped with a mechanical stirrer, thermocouple, nitrogen inlet and a reflux condenser, the product from part (c) (41.75 g), methylene chloride (375 ml) and water (2.7 ml) were added. Under nitrogen, tributyl phosphine (13.24 ml) was added to the reaction flask with thorough agitation at 18–26° C. The reaction mixture was stirred at 18–26° C. until the reaction was complete (1 to 4 hours) as judged by in-process HPLC analysis. Methanesulfonic acid (6.8 ml) was added to the mercaptan solution and the reaction mixture was heated at reflux with thorough stirring for 6 to 7 hours and at ambient temperature for 12 to 16 hours until the reaction was complete as judged by in-process HPLC analysis. The solvent of the reaction mixture was exchanged with methanol by distillation and the resulting methanol solution of [4S-(4α,7α,10aβ)]-octahydro-5-oxo-4-[(trifluoroacetyl)amino]-7H-pyrido[2,1-b] [1,3]thiazepine-7-carboxylic acid, methyl ester was treated with buffered (pH 10.5) 1M potassium carbonate solution (208 ml) maintaining the pH in the range of 10.4 to 10.8 at 40 to 45° C. The reaction mixture was stirred at 40 to 45° C. until the deprotection was judged complete by in-process HPLC analysis. The pH of the reaction mixture was adjusted to 5.8 to 6.5 by the addition of concentrated HCl (33.5 ml) at less than 36° C. Methanol was removed in vacuo at less than 37° C. until the volume of the quenched deprotection reaction mixture was 300 ml. Methylene chloride was added to the aqueous solution and the pH of the biphasic mixture was adjusted to 0.6 to 0.9 by the addition of concentrated HCl (7 ml). The phases were separated and the product rich aqueous layer was washed with additional methylene chloride (60 ml). The combined methylene chloride extracts were back washed with 3% HCl solution (60 ml) and the aqueous extract was combined with the product rich aqueous layer. Methylene chloride (80 ml) was added to the product-rich aqueous layer and the pH of the biphasic mixture was adjusted to 9.0 by the addition of 10N sodium hydroxide solution (19 ml) and then to pH 10.4 by the addition of 1N sodium hydroxide solution (3 ml). The phases were separated and the aqueous layer was extracted with methylene chloride (2×80 ml). The product rich methylene chloride layers were combined, and methanol (15 ml) and chlorotrimethylsilane were added. Ethyl acetate (50 ml) was added slowly (15 minutes) to the methylene chloride solution of the title compound at 34 to 37° C. and the mixture was stirred until crystallization was evident. Additional ethyl acetate (175 ml) was added to complete the crystallization. The resulting product slurry was cooled to 15 to 25° C., the slurry was stirred for at least one hour and the product was collected on a filter. The wet-cake was washed with ethyl acetate (2×50 ml) and the product was dried under vacuum (150 mm of Hg) at 45° C. for 16 hours to afford 25.2 g of title product as a white crystalline powder, m.p. 239° C. (decomposes).

IR (KBr), 3437 (w), 2950 (s), 1982 (w), 1757 (m), 1737 (s), 1665 (s), 1496 (m), 1445 (m), 1373 (m), 1281 (w), 1209 (m), 1066(w), 1004 (w) and 983 (w).

$^1$H-NMR: 300 MHz; $CD_3OD$: δ 1.55–1.80 (m, 3H), 2.0–2.5 (m, 5H), 3.0 (dd, 1H), 3.3 (m, 1H), 3.75 (s,3H), 5.15 (m, 1H) and 5.65 (m, 1H). $^{13}$C-NMR: 75 MHz; $CD_3OD$: δ 17.93, 25.75, 30.83, 30.91, 31.97, 52.38, 52.66, 52.35, 59.82, 171.84 and 172.68.

EXAMPLE 2

6,6-Dimethoxy-N-[N-(trifluoracetyl)-L-homocysteinyl]-L-norleucine, methyl ester (1→1') disulfide The product of Example 1(c) was also prepared according to the following procedure.

a) (S)-2-Amino-6,6-dimethoxyhexanoic acid, methyl ester

Under nitrogen, chlorotrimethyl silane (532 g) was added to a slurry of (S)-α-amino-1,3-dioxolane-2-pentanoic acid (380 g) and dimethyl sulfite (228 g) in methanol (4560 ml) to afford a homogeneous solution. Following the observation of an exotherm to 29° C., the solution was heated to 42° C., stirred at that temperature for 8 hours at about 22° C. for 16 hours. In process HPLC analysis showed that a 93 M % yield of product was obtained. A portion of the resulting solution containing 53.4 g of title product was cooled to −5 to −10 °C. with stirring and the apparent pH of the mixture was adjusted from −0.38 to about 8.32 by the slow careful addition of 32% methanolic potassium methoxide solution (2×100 ml). The pH of the mixture was further adjusted to 11.45 by the careful addition of potassium methoxide (16 ml) maintaining the temperature below 5° C. In process $^1$H NMR analysis of the product slurry indicated that the neutralization was complete. The solvent of the product slurry was exchanged with ethyl acetate (total 3160 ml) via a vacuum distillation at less than 30° C., concentrated to 400 ml volume, diluted with tert-butyl methyl ether (800 ml), cooled to 0° C., agitated for 30 minutes, and filtered. The filtrate was treated with calcium chloride dihydrate (135 g in 9 portions) until in-process GC assay indicated that ethylene glycol was absorbed by the calcium chloride dihydrate. The resulting slurry was filtered to afford a filtrate containing 49.7 g of title product.

b) 6,6-Dimethoxy-L-norleucine, methyl ester [S-(R*,R*)]-4,4-dithiobis[2-[(trifluoroacetyl)-amino]butanoate (2:1)

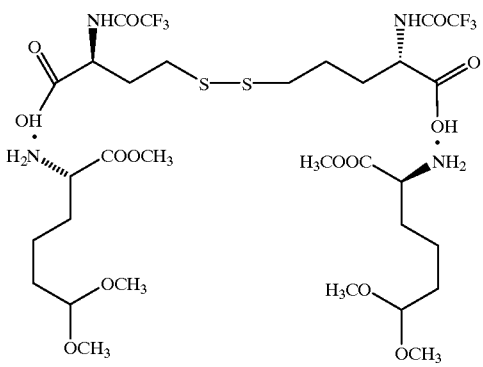

N-(Trifluoroacetyl)-L-homocysteine, (1→1')disulfide (55.8 g) was dissolved in ethyl acetate (200 ml) and the resulting solution was added to a tert-butyl methyl ether/ethyl acetate solution of (S)-2-amino-6,6-dimethoxy-hexanoic acid, methyl ester (about 49.7 g, 1787 ml of solution) over 10 minutes. The resulting mixture was stirred for one hour and the product slurry was filtered. The wet-cake was washed with tert-butyl methyl ether/ethyl acetate (2:1, 250 ml) and dried under vacuum at 30° C. to afford 98.0 g of title product; m.p. 129.1–129.7° C.

IR (KBr), 3317 (w), 2951 (br, w), 2143 (w), 1756 (s), 1702 (s), 1648 (s), 1551 (m), 1444 (w), 1390 (m), 1358 (m), 1170 (s), 1078(w), and 1057 (w).

Anal. Cal'd. for $C_{30}H_{52}F_6N_4O_{14}S_2$: C, 41.38; H, 6.02; F, 13.09; N, 6.43; S, 7.36 Found: C, 41.38; H. 5.99; F, 13.36; N, 6.34; S, 7.39.

c) 6,6-Dimethoxy-N-[N-(trifluoroacetyl)-L-homocysteinyl]-L-norleucine, methyl ester, (1→1')disulfide The product from part (b) (95 g); ethyl acetate (750 ml) and water (13.5 ml) were charged to a 3 l round bottomed flask equipped with an overhead stirrer, nitrogen inlet, thermocouple, and a temperature controller. Hydroxybenzotriazole hydrate (1.5 g), sodium sulfate (34.5 g) and water (3.5 ml) were added to the reaction mixture. The resulting solution was cooled to −6° C. and dicyclohexylcarbodiimide (49.1 g) was added to the reaction mixture. The reaction mixture was agitated at −2 to 2° C. until the reaction was judged complete by in-process HPLC analysis (5.6 hours). The reaction slurry was filtered and the wet-cake was rinsed with ethyl acetate (2×50 ml). The combined filtrates (925 ml) were washed with saturated sodium bicarbonate solution (125 ml) and saturated brine solution (125 ml). The resulting ethyl acetate solution of the title compound was concentrated to an oil. The oil was dissolved in ethyl acetate (900 ml), concentrated to an oil, and this oil was again dissolved in ethyl acetate (300 ml). Tert-butyl methyl ether (300 ml) was added and the resulting solution was polish filtered and the filter-cake was washed with 1:1 ethyl acetate/tert-butyl methyl ether (2×25 ml). Cyclohexane (400 ml) and seed crystals were added to the combined filtrates and the mixture was stirred for about 30 minutes. To the resulting thin slurry, cyclohexane (1800 ml) was added over 75 minutes. After 16 hours of stirring, the slurry was filtered through paper and the wet-cake was washed with a solution of ethyl acetate/tert-butyl methyl ether/cyclohexane (1:1:6, 175 ml). The wet-cake (194 g) was dried under vacuum at 20° C. and afforded 77.6 g of white title product; m.p. 111–112° C.

IR (KBr), 3290 (s), 3080 (w), 2945 (m), 2832 (w), 1740 (s), 1702 (s), 1659 (s), 1546 (s), 1445 (w), 1363 (w), 1196 (s), 1126 (m, shoulder), 1073 (w), and 1051 (w).

Anal. Calc'd. for $C_{30}H_{48}F_6N_4O_{12}S_2$: C, 43.16; H, 5.80; F, 13.65; N, 6.71; S, 7.68. Found: C, 4327; H. 5.76; F, 13.79; N, 6.62; S, 7.78.

EXAMPLE 3

[4S-(4α,7α,10aβ)]-Octahydro-5-oxo-4-[[(phenylmethoxy)carbonyl]amino]-7H-pyrido-[2,1-b][1,3]thiazepine-7-carboxylic methyl ester

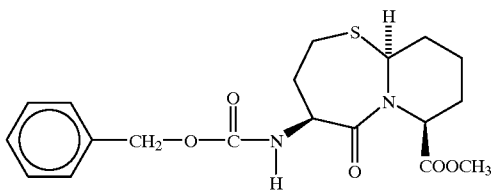

a) N-[(Phenylmethoxy)carbonyl]-L-homocysteine, (1→1')-disulfide

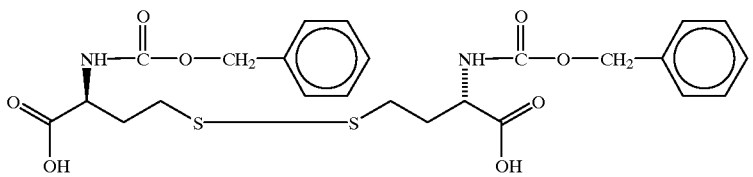

L-Homocystine (15.0 g) was dissolved in water (90 ml) by the addition of 1N sodium hydroxide solution (137 ml) and the resulting pH 13.3 solution was cooled to 5° C. Benzyl chloroformate (21 ml) was slowly added (over 135 minutes) while maintaining the pH of the reaction mixture at about 13 by the addition of 1N sodium hydroxide solution (192 ml). Once the reaction was judged to be complete by HPLC analysis, it was extracted with methyl isobutyl ketone (300 ml and 400 ml). The emulsion which formed during the second extraction was broken by the addition of saturated brine solution (60 ml) and the phases were separated. Methanol (50 ml) was added to the rich aqueous solution and the pH was adjusted to about 2 by the addition of concentrated hydrochloric acid solution (24 ml). The resulting product slurry was filtered, washed with water (100 ml) and 1:5 methanol/water (vol/vol), and was dried in vacuo for 18 hours to afford 28.6 g of title product as a crystalline solid; m.p. 110–115° C.

IR (KBr), 3544 (w, shoulder), 3329 (m), 3032 (w), 2955 (w), 1690 (s), 1534 (s), 1439 (m), 1414 (w), 1347 (w), 1250 (s), 1055 (m) and 912 (w).

b) 6,6-Dimethoxy-N-[N-[(phenylmethoxy)carbonyl]-L-homocysteinyl]-L-norleucine, methyl ester, (1→1')-disulfide

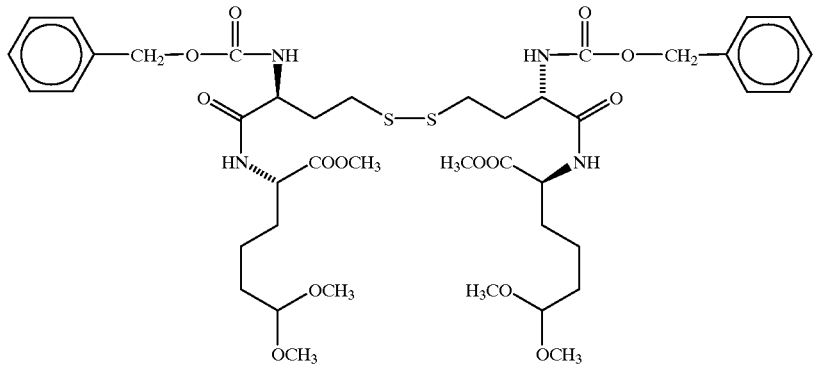

The product from part (a) (3.0 g) was added to a tetrahydrofuran (45 ml) solution of (S)-2-amino-6,6-dimethoxyhexanoic acid, methyl ester (2.4 g) cooled to −4° C. Dicyclohexylcarbodiimide (2.53 g) was added to the resulting solution in one portion and the reaction mixture was stirred mechanically under a nitrogen atmosphere for 18 hours until it was judged to be complete by HPLC analysis. The precipitated dicyclohexylurea was removed by filtration and the wet-cake was washed with tetrahydrofuran (15 ml). The combined filtrates were diluted with ethyl acetate (150 ml), washed with pH 3.4 phosphate buffer (40 ml) and saturated sodium bicarbonate solution (2×60 ml). the organic layer was concentrated to an oil in vacuo, redissolved in ethyl acetate (45 ml) and diluted with sufficient hexane to crystallize the product. After stirring the slurry at ambient temperature for one hour the product wet-cake was collected on a filter and was washed with (1:2.5) ethyl acetate/heptane (80 ml). the wet-cake was dried in vacuo to afford 4.22 g of the title product as white crystals; m.p. 109–110° C.

IR (KBr), 3309 (s), 3063 (w), 3032 (w), 2955 (m, 1742 (s) 1696 (s), 1655 (s), 1537 (s), 1439 (w), 1388 (w), 1260 (m), 1132 (m) and 1056 (m).

c) [4S-(4α,7α,10aβ)]-Octahydro-5-oxo-4-[[(phenylmethoxy)carbonyl]amino]-7H-pyrido-[2,1-b][1,3]thiazepine-7-carboxylic acid, methyl ester D,L-Dithioerythritol(0.06 g) was added to a nitrogen sparged methyl acetate solution of the product from part (b) (0.295 g) cooled to −7° C. Sodium methoxide solution (25% in methanol, 0.02 ml) was added to the reaction mixture and it was stirred for about 30 minutes until it was judged complete by HPLC analysis. The monomer solution was stirred at −7° C. for another 60 minutes and chlorosulfonic acid (0.018 ml) was added. Stirring was continued at −7° C. for 4 hours and then the reaction mixture was stored in the freezer for 16 hours. The reaction mixture was washed with 3% hydrochloric acid solution (2×10 ml) and saturated sodium bicarbonate solution (2×8 ml). The organic layer was dried and concentrated to a residue affording 0.31 g of title product as an oil (94.2 M %). HPLC: Tr=6.02 min (UV 210 nm): YMC basic 5 micron particle size, 4.6×250 mm, 40 v/v % (0.01 M potassium dihydrogen phosphate solution, pH 4.0): 60 v/v % acetonitrile, 20 microliter injection volume eluted at 1.0 ml/min. Dissolved 11.8 mg in 50 ml of mobile phase.

EXAMPLE 4

[4S-(4α,7α,10aβ)]-4-Aminooctahydro-5-oxo-7H-pyrido-[2,1-b] [1,3]thiazepine-7-carboxylic acid, methyl ester, hydrochloride a) N-Formyl-L-homocysteine, (1→1')-disulfide

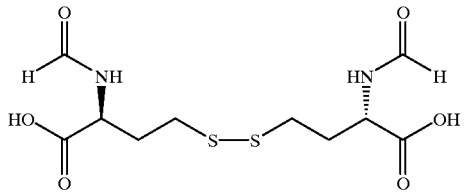

L-Homocystine (5.37 g) was dissolved in formic acid (23 ml) to afford a viscous solution which was cooled to 5° C. in an ice bath. Acetic anhydride (11.2 ml) was added to this solution dropwise over about 4 minutes and the temperature of the reaction mixture rose to about 10° C. The reaction mixture was stirred for 6 hours until it was judged to be complete by HPLC analysis. The reaction mixture was quenched by the addition of ice water (10 ml) and was then concentrated to a white residue on a rotary evaporator. The white residue was further dried under vacuum at ambient temperature. The resulting dry white powder (6.9 g) was suspended in refluxing chloroform (40 ml) and denatured ethanol (SDA 35A, 8 ml) was added. The mixture was allowed to cool to about 20° C., the product was filtered and the wet-cake was washed with cold chloroform. After drying in vacuo the title product was isolated as a white crystalline powder (5.85 g, 90 M %).

1H-NMR: 300 MHz; $D_6$DMSO; δ 1.8–2.0 (m, 2H), 2.0–2.2 (m, 2H), 2.8 (br s, 4H), 4.4 (br s, 2H), 8.1 (s, 2H), 8.4 (d, 2H) and 12.6–13.0 (br s, 2H).

b) N-(N-Formyl-L-homocysteinyl)-6,6-dimethoxy-L-norleucine, methyl ester, (1→1')-disulfide

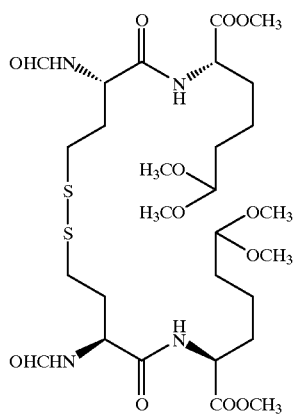

(S)-2-Amino-6,6-dimethoxyhexanoic acid, methyl ester (2.05 g) was added to a tetrahydrofuran (45 ml) slurry of the product from part (a) (1.62 g) at 22° C. The resulting thick, sticky slurry was agitated for about 10 minutes, and dicyclohexylcarbodiimide (2.29 g) was added. After about 15 minutes of agitation the sticky slurry was replaced with a finely divided white powder as the reaction progressed. The reaction was agitated for 15 hours until it was judged complete by TLC analysis. The precipitated dicyclohexylurea was removed by filtration and the wet-cake was washed with tetrahydrofuran (10 ml). The combined filtrates were concentrated on a rotary evaporator and the residue was dissolved in methylene chloride (100 ml). The resulting solution was washed with water (50 ml), 5% citric acid (50 ml) and 5% sodium bicarbonate solution (50 ml). The organic layer was dried over magnesium sulfate and concentrated to dryness on a rotary evaporator affording the product (3.82 g) as a sticky foam. The foam was purified by radial chromatography using a solvent gradient of 5 volume % methanol in ethyl acetate to 10 volume % methanol in ethyl acetate to afford 2.83 g (81 M %) of the product as a yellow glass. The resulting yellow glass was dissolved in refluxing ethyl acetate, and hexane (30 ml) was added to the cloud point. The resulting mixture was stirred at ambient temperature for 16 hours, the product was filtered and the wet-cake was washed with hexane (2×4 ml). The product was dried in vacuo to afford 1.3 g (37.2 M %) of the product as an amorphous solid; m.p. 88–92° C.

IR (KBr), 3319 (s) 2940 (m), 2853 (w, shoulder), 2116 (m), 1747 (s), 1649 (s), 1547 (m), 1439 (m), 1383 (m), 1219 (m), 1137 (m) and 1060 (w).

c) [4S-(4α,7α,10aβ)]-Octahydro-5-oxo-4-(N-formyl)-7H-pyrido[2,1-b] [1,3]thiazepine-7-carboxylic acid, methyl ester

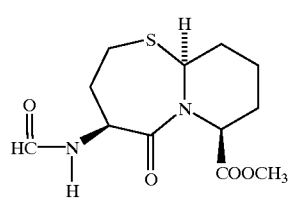

D,L-Dithioerythritol (0.24 g) was added to a nitrogen sparged methyl acetate solution of the product from part (b) (1.05 g) cooled to −10° C. Sodium methoxide solution (25% in methanol, 0.07 ml) was added to the reaction mixture and it was stirred for about 16 hours. Following HPLC analysis of the reaction mixture, additional D,L-dithioerythritol (0.03 g) and sodium methoxide solution (25% in methanol, 0.01 ml) were added and the reaction mixture was stirred for one hour. Following HPLC analysis of the reaction mixture, additional D,L-dithioerythritol (0.06 g) and sodium methoxide solution (25% in methanol, 0.01 ml) were added and the reaction mixture was stirred until it was judged complete by HPLC analysis. The monomer solution was washed with 0.01 M sulfuric acid (10 ml) and saturated sodium bicarbonate solution (10 ml). The organic layer was concentrated on a rotary evaporator to afford the crude monomer as a thick liquid (0.84 g, 80M %). The monomer was dissolved in methyl acetate and the resulting solution was sparged with nitrogen before Amberlyst 15® (2 g) was added. The reaction mixture was stirred at 10° to 15° C. until the reaction was complete (16 hours) as judged by HPLC analysis. The resin was filtered-off and washed with methyl acetate (15 ml). The filtrates were washed with saturated sodium bicarbonate solution (2×10 ml) and the aqueous wash was back extracted with methyl acetate (2×5 ml). The combined organic layers were concentrated in vacuo to afford 0.6 g (87 M %) of the title product as a residue.

$^1$H-NMR: 300 MHz; CDCl$_3$: δ 1.7–2.2 (m, 6H), 2.3–2.6 (m, 2H), 2.9–3.0 (m, 1H), 3.3–3.4 (m, 1H), 3.8 (s, 3H), 5.15 (m, 1H), 5.25 (m, 1H), 5.35 (m, 1H), 7.2 (br s, 1H) and 8.2 (s, 1H).

$^{13}$C-NMR: 75 MHz; CDCl$_3$; 16.99, 24.73, 31.13, 32.60, 49.89, 51.09, 52.31, 59.05, 160.08, 171.21 and 172.59. HPLC: Tr =8.42 min. (UV 210 nm); YMC basic 5 micron particle size, 4.6×250 mm, 75 v/v % (0.01 M potassium dihydrogen phosphate solution, pH 4.0): 25 v/v % acetonitrile, 20 microliter injection volume eluted at 1.0 ml/min.

d) [4S-(4α,7α,10aβ)]-4-Aminooctahydro-5-oxo-7H-pyrido [2,1-b] [1,3]thiazepine-7-carboxylic acid, methyl ester, hydrochloride Concentrated hydrochloric acid (0.4 ml) was added to a methanol solution (8 ml) of the product from part (c) (0.6 g) and the solution was diluted with water (0.4 ml). The reaction mixture was stirred at ambient temperature until it was judged complete (72 hours) by HPLC analysis. The methanol was removed in vacuo and the residue was dissolved in 1N hydrochloric acid (10 ml) and washed with methylene chloride (2×6 ml). The aqueous layer was basified with potassium carbonate to pH 10.5 and the solution was extracted with methylene chloride (6×8 ml). The organic extracts were concentrated in vacuo to give 0.37 g (49 M %) of title product as a residue.

$^1$H-NMR: 300 MHz; CDCl$_3$; δ 1.6–2.1 (m, 6H), 2.2–2.5 (m, 2H), 3.05 (m, 2H), 3.75 (s, 3H), 4.1 (dd, 1H), 5.25 (m, 1H), and 5.4 (m, 1H).

$^{13}$C-NMR: 75 MHz; CDCl$_3$; 16.96, 25.04, 30.61, 30.83, 35.19, 51.10, 52.16, 52.92, 57.71, 171.79 and 177.12. HPLC: Tr =3.86 min. (UV 210 nm): YMC basic 5 micron particle size, 4.6×250 mm, 75 v/v % (0.01 M potassium dihydrogen phosphate solution, pH 4.0): 25 v/v % acetonitrile, 20 microliter injection volume eluted at 1.0 ml/min.

EXAMPLE 5

[4S-(4α,7α, 10aβ)]-Octahydro-5-oxo-4-[(trifluoroacetyl)amino]-7H-pyrido-[2,1-b] [1,3]thiazepine-7-carboxylic acid, methyl ester

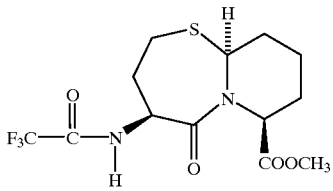

The product from Example 1(c) (2.0 g) was dissolved in methylene chloride/methanol (20 ml, 8:2) and zinc metal powder (0.45 g) was added. To this suspension methanesulfonic acid (2.3 g, 10 eq.) was added and the mixture was stirred at room temperature until it was judged complete by HPLC assay. Typically, the reaction takes about one to two hours to go to completion. The product stream was washed with water (10 ml) and the methylene chloride solution was concentrated to dryness to afford the desired product as an oil (1.1667 g, 68.7M %).

This oil can be converted to [4S-(4α,7α,10aβ)]-4-aminooctahydro-5-oxo-7H-pyrido[2,1-b][1,3]thiazepine-7-carboxylic acid, methyl ester, hydrochloride by dissolving in methanol and reacting with potassium carbonate solution followed by concentrated hydrochloric acid as described in Example 1(d).

Example 6

6,6-Dimethoxy-N-[N-trifluoroacetyl)-L-homocysteinyl]-L-norleucine, methyl ester, (1→1')-disulfide The product of Examples 1(c) and 2 was also prepared as follows.

a) N-(Trifluoroacetyl)-L-homocysteine, (1→1')-disulfide

The product of Example 1(a) was also prepared as follows.

Under nitrogen, L-homocystine (13.34 g) and 32% potassium methoxide in methanol (22.97 g) were charged to a 500 ml three-neck round bottom flask equipped with an overhead stirrer, thermometer, nitrogen inlet, vent, and an addition funnel. The addition funnel was rinsed with methanol (10.2 g) and the rinse was added to the mixture. The resulting slurry was thoroughly stirred with rapid agitation at room temperature for 30 to 40 minutes to obtain a clear solution. Ethyl trifluoroacetate (15.2 g) was added to the resulting solution at a rate which maintained the reaction temperature at 35 to 40° C. The additional funnel was rinsed with methanol (2.7 g) and the rinse was added to the reaction mixture. The reaction mixture was heated at 38 to 40° C. until completion as judged by in-process HPLC. Methanol (2.7 g) was charged to the reaction mixture and it was cooled to room temperature (about 25° C.). Acidified aqueous brine [143.4 g, prepared by dissolving concentrated hydrochloric acid (12 g) and sodium chloride (1.44 g) in water (130 g)] and n-butyl acetate (100 ml) were added to the mixture. The phases were separated and the organic phase was washed consecutively with 12 and 24% brine solutions (60 g each). The washed organic phase was diluted with n-butyl acetate (60 ml) to a total volume of 160 ml and then concentrated at 55 to 60° C. until the water content of the distillate was less than 0.2%. After cooling to about 25° C., heptanes (80 ml) and some seed crystals (30 mg) were added to the product solution. Additional heptanes (200 ml) were added to the crystallization mixture slowly over 60 minutes. The resulting slurry was stirred at about 25° C. for 1 to 4 hours and the product was collected on a filter. The product wet-cake was washed with 9:1 heptanes/n-butyl acetate (50 ml) and then with heptanes (50 ml) before it was vacuum dried (25 torr, 45° C.) overnight (16–18 hours to afford 20.7 of title product.

Analytical data: $^1$H-NMR: 360 MHz; D$_6$DMSO: δ 2.1 (m, 2H), 2.4 (m, 2H), 2.9 (m, 4H), 4.5 (m, 2H) and 9.9 (s, 2H).

HPLC: Tr=5 min. (UV 210 nm): E. Merck Lichrosorb NH$_2$, 250×5 mm, 5 micron, 25 v % 0.025 M NH$_4$OAc, pH=4.5: 75 v % acetonitrile, 20 microliter injection volume eluted at 1.0 ml/min.

b) (S)-2-Amino-6,6-dimethoxyhexanoic acid, methyl ester

The product of Example 1(b) was also prepared as follows.

Under nitrogen, (S)-α-amino-1,3-dioxolane-2-pentanoic acid (25.0 g), methanol (300 ml) and dimethyl sulfite (12.32 ml) were added to a 500 ml three-neck round bottom flask equipped with a mechanical stirrer, thermocouple, heater, nitrogen inlet and bubbler. Chlorotrimethylsilane (41.95 ml) was added to the resulting slurry which was heated at 40° C. for 8 hours to give (S)-2-amino-6,6-dimethoxyhexanoic acid, methyl ester, hydrochloride salt. After cooling to about 25° C., the hydrochloride salt solution was neutralized by addition to a slurry of potassium bicarbonate (52.15 g) in methanol (100 ml) at a rate which maintained the pH above 7 (total addition time about 1 hour). n-Butyl acetate (200 ml) was added and the slurry was concentrated under vacuum (110 to 30 torr) keeping the temperature below 30° C. to remove methanol. The neutralized slurry of (S)-2-amino-6,6-dimethoxyhexanoic acid, methyl ester was held at 0–5° C. while the following step was performed.

c) N-(Trifluoroacetyl)-L-homocysteine, (1→1')disulfide, diacid chloride

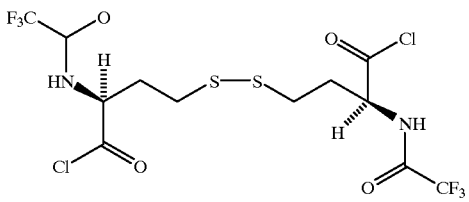

Under nitrogen, N-(trifluoroacetyl)-L-homocysteine, (1→1')disulfide (25.34 g), ethyl acetate (150 ml) and n-butyl acetate (75 ml) were charged to a 500 ml three-neck round bottom flask equipped with a mechanical agitator, thermocouple, heater, nitrogen inlet and bubbler. The resulting solution was cooled to −10° C. (Chloromethylene) dimethylammonium chloride (Vilsmeier Reagent, 16.9 g) was charged to the resulting solution and it was stirred at −5 to −11° C. until the reaction was complete as judged by in-process HPLC analysis.

d) 6,6-Dimethoxy-N-[N-(trifluoroacetyl)-L-homocysteinyl]-L-norleucine, methyl ester (1→1') disulfide A cooled solution (0–5° C.) of potassium bicarbonate (22.03 g) in water (250 ml) was added to the n-butyl acetate slurry of (S)-2-amino-6,6-dimethoxyhexanoic acid, methyl ester from part (b) and the pH of the vigorously agitated mixture was adjusted to 8.5 by the addition of 20 w/v % of aqueous potassium carbonate solution. The diacid chloride solution from part (c) was then slowly added (over 1 to 2 hours) to the vigorously stirred biphasic mixture of (S)-2-amino-6,6-dimethoxyhexanoic acid, methyl ester at −1 to 5° C. maintaining the pH at 8.0–8.5 throughout the diacid chloride addition using 20% aqueous potassium carbonate. The diacid chloride addition funnel was rinsed with cold (0 to 5° C.) ethyl acetate (12.5 ml) and the rinse was added to the reaction mixture. Thirty minutes after the addition of the diacid chloride was completed, the phases were separated and the organic phase was washed with water (2×250 ml). The rich organic phase was concentrated under vacuum to about 250 ml volume at 60 to 70° C. followed by the addition of peanut oil (14.5 ml) and heptanes (550 ml). The crystallization mixture was stirred at 60 to 70° C. for at least 30 minutes to permit good crystal formation. The crystal slurry was subjected to an alternating cooling/heating/cooling protocol and after cooling to 20 to 25° C. the product was collected on a filter. The resulting wet-cake was washed with 1:4 n-butyl acetate/heptanes (2×130 ml) and heptanes (130 ml). The product wet-cake was dried under vacuum at less than 45° C. to afford 41 g of the desired product as a white solid having an HPLC area percent of 91–94.

Analytical data: $^1$H-NMR: 360 MHz; $CDCl_3$: δ 1.4 (m, 4H), 1.6 (m, 4H), 1.8 (m, 2H), 1.9 (m, 2H), 2.2 (m, 2H), 2.3 (m, 2H), 2.8 (m, 4H), 3.3 (s, 12H), 3.8 (s, 6H), 4.3 (d, 2H), 4.5 (m, 2H), 4.9 (m, 2H), 7.4 (d, 2H) and 7.7 (d, 2H).

What is claimed is:

1. A compound of the formula

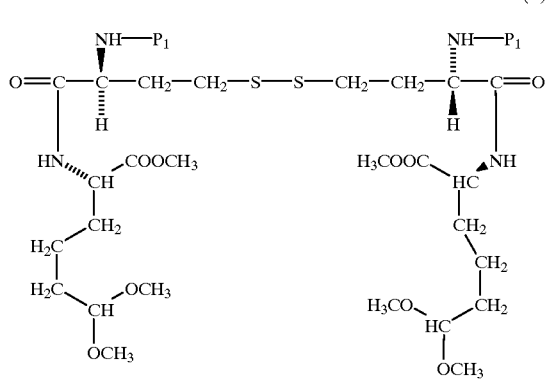

(II)

wherein $P_1$ is a nitrogen protecting group.

2. A compound of claim 1 wherein $P_1$ is selected from the group consisting of trifluoroacetyl, phenylmethoxycarbonyl, formyl, phthalimido, and t-butoxycarbonyl.

3. The compound of claim 1 wherein $P_1$ is trifluoroacetyl.

4. The compound of claim 1 wherein $P_1$ is phenylmethoxycarbonyl.

5. The compound of claim 1 wherein $P_1$ is formyl.

6. A disalt of the formula

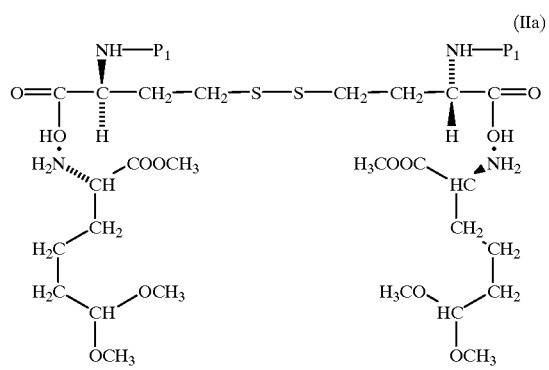

(IIa)

wherein $P_1$ is a nitrogen protecting group.

7. A compound of claim 6 wherein $P_1$ is selected from the group consisting of trifluoroacetyl, phenylmethoxycarbonyl, formyl, phthalimido, and t-butoxycarbonyl.

8. A compound of claim 7 wherein $P_1$ is trifluoroacetyl.

9. A process for preparing the compound of the formula

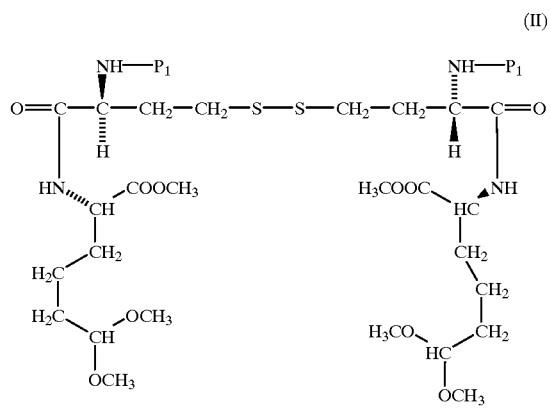

(II)

wherein $_1$ is a nitrogen protecting group which comprises:

a) reacting L-homocystine to introduce the group $P_1$ on both nitrogens and give the disulfide intermediate of the formula

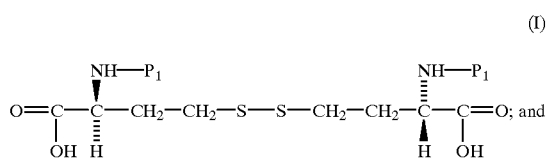

(I)

reacting the disulfide of formula I with (S)-2-amino-6,6-dimethoxyhexanoic acid, methyl ester in the presence of a coupling reagent to give the desired product of formula II; or b) reacting L-homocystine to introduce the group $P_1$ on both nitrogens and give the disulfide intermediate of the formula

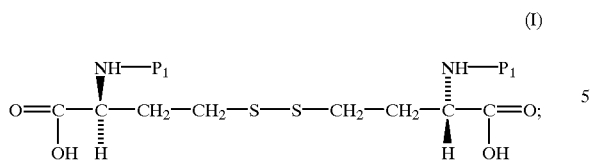

converting the disulfide intermediate of formula I to an activated form; and reacting the activated form of the disulfide of formula I with (S)-2-amino-6,6-dimethoxyhexanoic acid, methyl ester to give the desired product of formula II; or c) reacting L-homocystine to introduce the group $P_1$ on both nitrogens and give the disulfide intermediate of the formula

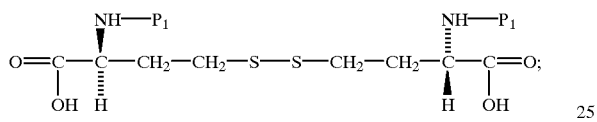

reacting the disulfide of formula I with (S)-2-amino-6,6-dimethoxyhexanoic acid, methyl ester to give the disalt of the formula

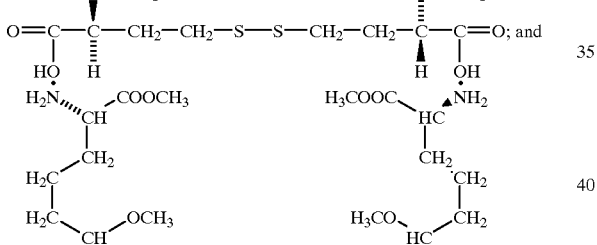

treating the disalt of formula IIa with a coupling reagent to give the desired product of formula II.

10. The process of claim 9(a) wherein:

L-homocystine is reacted with ethyl trifluoroacetate to give the intermediate of formula I which is then reacted with (S)-2-amino-6,6-dimethoxyhexanoic acid in the presence of a coupling reagent wherein the coupling reagent is dicyclohexylcarbodiimide.

11. The process of claim 9(a) wherein:

L-homocystine is reacted with benzyl chloroformate to give the intermediate of formula I which is then reacted with (S)-2-amino-6,6-dimethoxyhexanoic acid in the presence of a coupling reagent wherein the coupling reagent is dicyclohexylcarbodiimide.

12. The process of claim 9(a) wherein:

L-homocystine is reacted with formic acid and acetic anhydride to give the intermediate of formula I which is then reacted with (S)-2-amino-6,6-dimethoxyhexanoic acid in the presence of a coupling reagent wherein the coupling reagent is dicyclohexylcarbodiimide.

13. The process of claim 9(b) wherein:

L-homocystine is reacted with ethyl trifluoroacetate to give the disulfide intermediate of formula I and the resulting disulfide of formula I is treated with (chloromethylene) dimethylammonium chloride to give the corresponding acid chloride which is then reacted with (S)-2-amino-6,6-dimethoxyhexanoic acid, methyl ester to give the desired product of formula II.

14. The process of claim 9(c) wherein:

L-homocystine is reacted with ethyl trifluoroacetate to give the disulfide of formula I which is then reacted with (S)-2-amino-6,6-dimethoxyhexanoic acid, methyl ester to give the disalt of formula IIa and the disalt of formula IIa is treated with dicyclohexylcarbodiimide to give the desired product of formula II.

15. The process of preparing the N-protected lactam of the formula

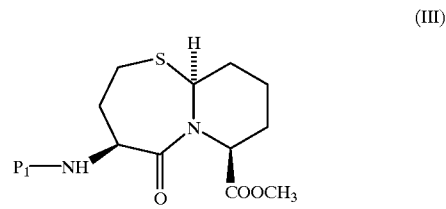

wherein $P_1$ is a nitrogen protecting group which comprises:

a) reacting the product of the formula

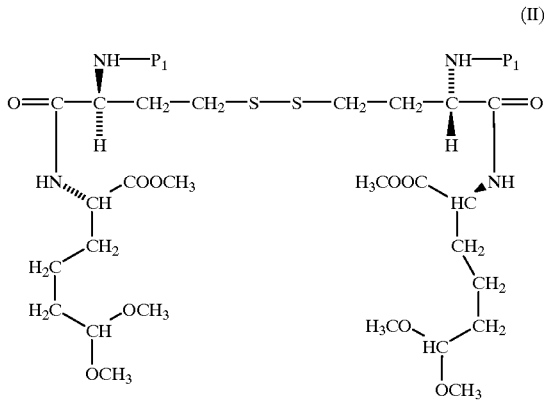

with a reagent that cleaves the disulfide bond; and b) subjecting the monomer from step (a) to an acid catalyzed cyclization reaction to give the desired product.

16. The process of claim 15 wherein:

the disulfide of formula II is treated with a bismercaptan, a phosphine reducing agent, a phosphite reducing agent, or zinc metal powder to cleave the disulfide bond.

17. The process of claim 16 wherein:

the disulfide of formula II is treated with tributyl phosphine.

18. The process of preparing the N-protected lactam of the formula (III)

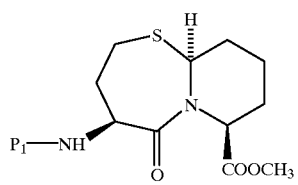

wherein $P_1$ is a nitrogen protecting group which comprises:
ai) reacting L-homocystine to introduce the group $P_1$ on both nitrogens and give the intermediate of the formula (I)

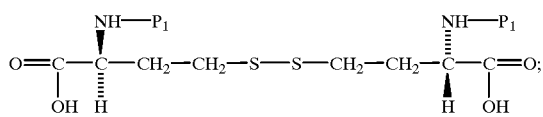

aii) reacting the disulfide of formula I with (S)-2-amino-6,6-dimethoxyhexanoic acid, methyl ester in the presence of a coupling reagent to give the compound of the formula (II)

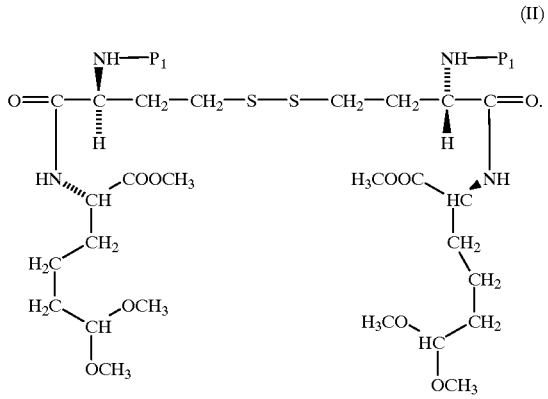

aiii) reacting the disulfide of formula II with a reagent that cleaves the disulfide bond; and
aiv) subjecting the monomer from part (aiii) to an acid catalyzed cyclization reaction to give the desired product; or
bi) reacting L-homocystine to introduce the group $P_1$ on both nitrogens and give the intermediate of the formula (I)

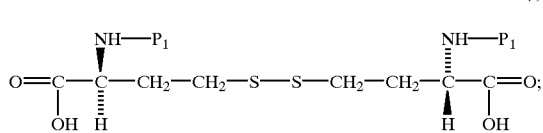

bii) converting the disulfide of formula I to an activated form;

biii) reacting the activated disulfide from part (bii) with (S)-2-amino-6,6-dimethoxyhexanoic acid, methyl ester to give the compound of the formula (II)

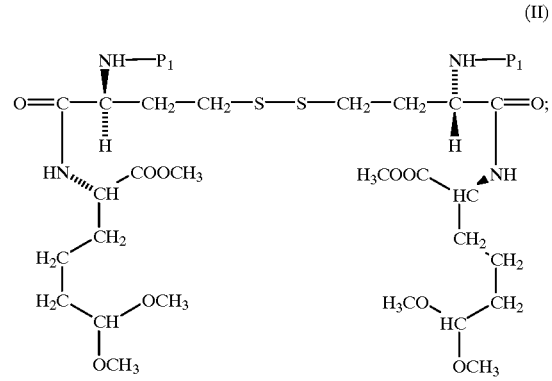

biv) reacting the disulfide of formula II with a reagent that cleaves the disulfide bond; and
bv) subjecting the monomer from part (biv) to an acid catalyzed cyclization reaction to give the desired product; or
ci) reacting L-homocystine to introduce the group $P_1$ on both nitrogens and give the intermediate of the formula (I)

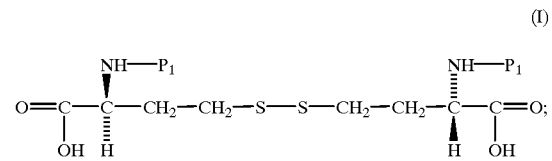

cii) reacting the disulfide of formula I with (S)-2-amino-6,6-dimethoxyhexanoic acid, methyl ester to give the disalt of the formula (IIa)

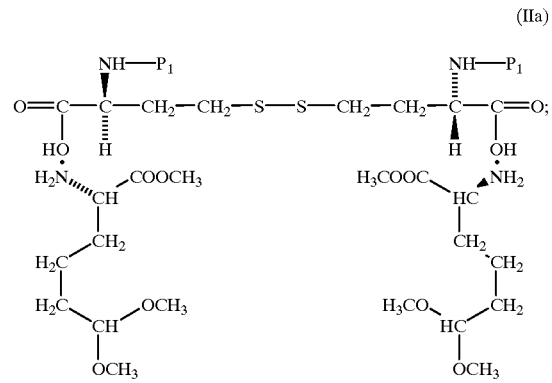

ciii) treating the disalt of formula IIa with a coupling reagent to give the compound of the formula (II)

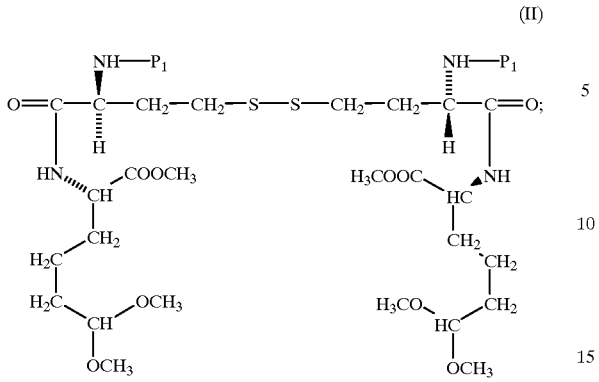

civ) reacting the disulfide of formula II with a reagent that cleaves the disulfide bond; and cv) subjecting the monomer from part (civ) to an acid catalyzed cyclization reaction to give the desired product.

19. The process of claim 18 wherein:

L-homocystine is treated with ethyl trifluoroacetate, benzyl chloroformate, or formic acid and acetic anhydride in step (ai), (bi), or (ci) and the disulfide of formula II is treated with tributyl phosphine in step (aiii), (biv) or (civ).

20. The process of preparing [4S-(4α,7α,10aβ)]-4-aminooctahydro-5-oxo-7H-pyrido[2,1-b][1,3]thiazepine-7-carboxylic acid, methyl ester or a salt thereof which comprises:

a) reacting the disulfide of the formula (II)

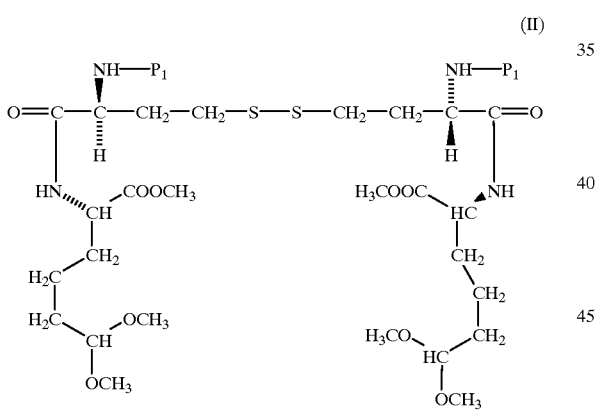

with a reagent that cleaves the disulfide bond;

b) subjecting the monomer from part (a) to an acid catalyzed cyclization reaction to give the N-protected lactam of the formula (III)

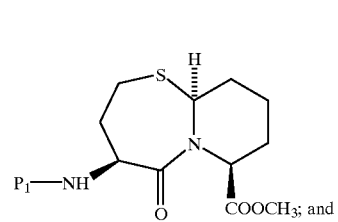

c) treating the N-protected lactam of formula III to remove the $P_1$ protecting group and give the desired product which can be optionally converted to a salt.

21. The process of claim 20 wherein:

the disulfide of formula II is treated with dithiothreitol, dithioerithritol, tributyl phosphine, or zinc metal powder in step (a) to cleave the disulfide bond.

22. The process of preparing [4S-(4α,7α,10aβ)]-4-aminooctahydro-5-oxo-7H-pyrido[2,1-b][1,3]thiazepine-7-carboxylic acid, methyl ester or a salt thereof which comprises:

ai) reacting L-homocystine to introduce the group $P_1$ on both nitrogens and give the intermediate of the formula (I)

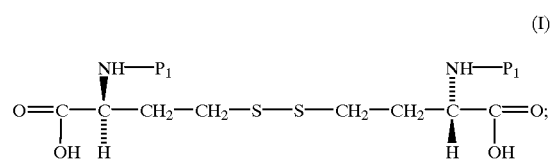

aii) reacting the disulfide of formula I with (S)-2-amino-6,6-dimethoxyhexanoic acid, methyl ester in the presence of a coupling reagent to give the compound of the formula (II)

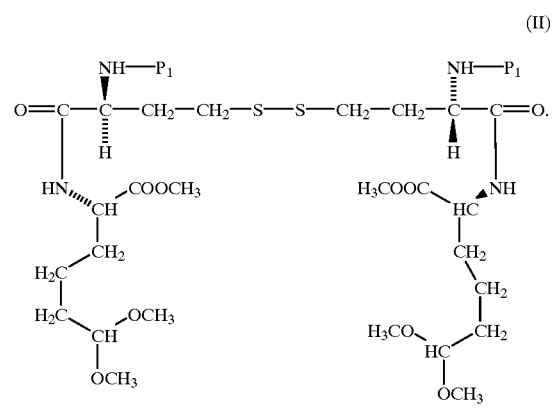

aiii) reacting the disulfide of formula II with a reagent that cleaves the disulfide bond;

aiv) subjecting the monomer from step (aiii) to an acid catalyzed cyclization reaction to give the N-protected lactam of the formula (III)

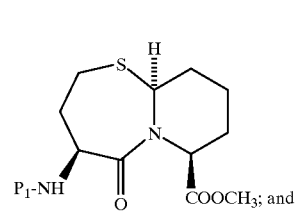

av) treating the N-protected lactam of formula III to remove the $P_1$ protecting group and give the desired product which can be optionally converted to a salt; or bi) reacting L-homocystine to introduce the group $P_1$ on both nitrogens and give the intermediate of the formula

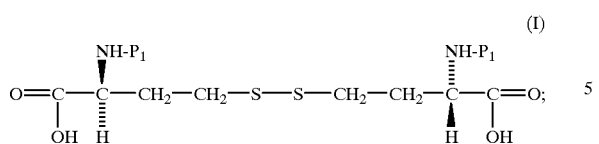
(I)

bii) converting the disulfide of formula I to an activated form;

biii) reacting the activated disulfide from step (bii) with (S)-2-amino-6,6-dimethoxyhexanoic acid, methyl ester to give the compound of the formula

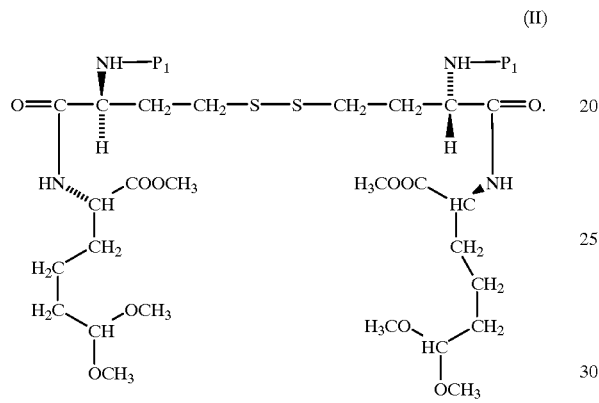
(II)

biv) reacting the disulfide of formula II with a reagent that cleaves the disulfide bond;

bv) subjecting the monomer from step (biv) to an acid catalyzed cyclization reaction to give the N-protected lactam of the formula

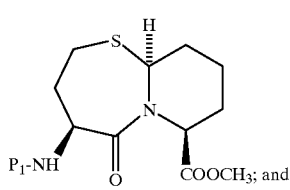
(III)

bvi) treating the N-protected lactam of formula III to remove the $P_1$ protecting group and give the desired product which can be optionally converted to a salt; or ci) reacting L-homocystine to introduce the group $P_1$ on both nitrogens and give the intermediate of the formula

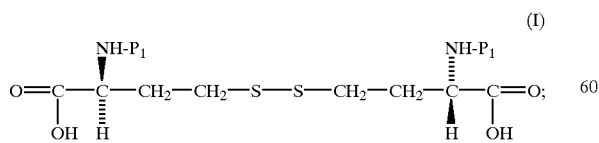
(I)

cii) reacting the disulfide of formula I with (S)-2-amino-6,6-dimethoxyhexanoic acid, methyl ester to give the disalt of the formula

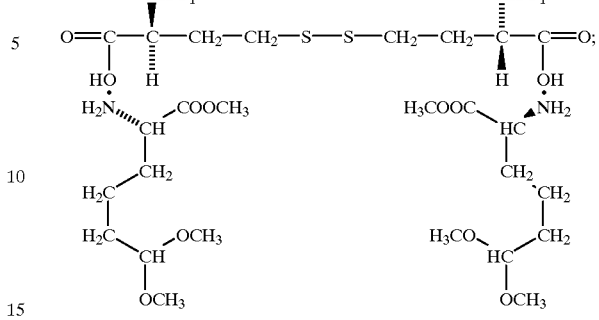
(IIa)

ciii) treating the compound of formula IIa with a coupling reagent to give the disalt of the formula

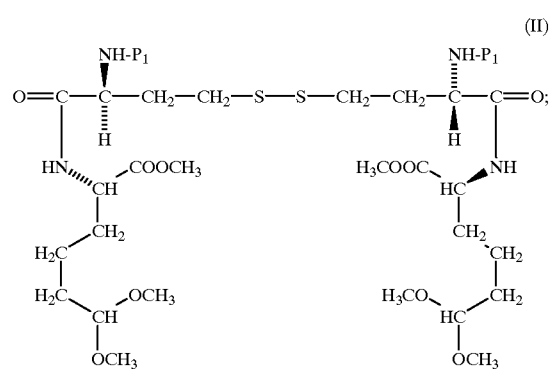
(II)

civ) reacting the disulfide of formula II with a reagent that cleaves the disulfide bond;

cv) subjecting the monomer from part (civ) to an acid catalyzed cyclization reaction to give the N-protected lactam of the formula

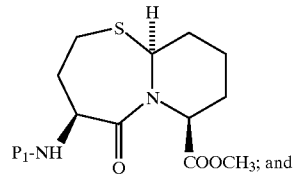
(III)

cvi) treating the N-protected lactam of formula III to remove the $P_1$ protecting group and give the desired product which can be optionally converted to a salt.

23. The process of claim 22 wherein:

L-homocystine is reacted with ethyl trifluoroacetate, benzyl chloroformate, or formic acid and acetic anhydride in step (ai), (bi) or (ci);

the coupling reagent in step (aii) or (ciii) is dicyclohexylcarbodiimide; and the disulfide of formula II is treated with dithiothreitol, dithioerithritol, tributyl phosphine, or zinc metal powder in step (aiii), (biv) or (civ).

24. The process of preparing [4S-(4α,7α,10aβ)]-4-aminooctahydro-5-oxo-7H-pyrido[2,1-b][1,3]thiazepine-7-carboxylic acid, methyl ester, hydrochloride which comprises ai) reacting L-homocystine with ethyl trifluoroacetate, benzyl chloroformate or formic acid and acetic anhydride to give the compound of the formula

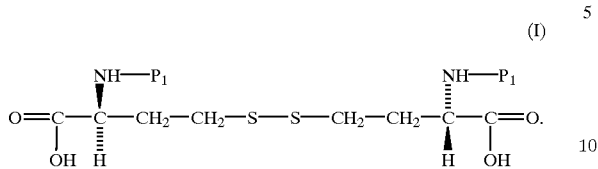
(I)

wherein $P_1$ is trifluoroacetyl, phenylmethoxycarbonyl or formyl;

aii) reacting the disulfide of formula I with (S)-2-amino-6,6-dimethoxyhexanoic acid, methyl ester in the presence of dicyclohexylcarbodiimide to give the compound of the formula

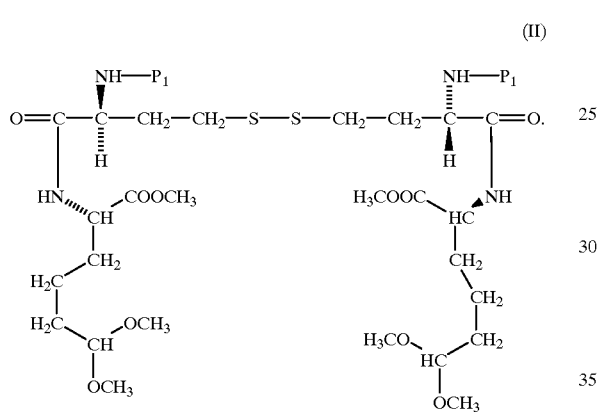
(II)

aiii) reacting the disulfide of formula II with tributyl phosphine to cleave the disulfide bond;

aiv) subjecting the monomer from step (aiii) to an acid catalyzed cyclization reaction to give the N-protected lactam of the formula

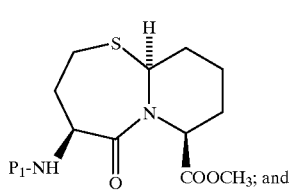
(III)

av) treating the N-protected lactam of formula III with potassium carbonate followed by hydrochloric acid when $P_1$ is trifluoroacetyl, or treating the N-protected lactam of formula III with iodotrimethylsilane followed by hydrochloric acid when $P_1$ is phenylmethoxycarbonyl, or treating the N-protected lactam of formula III with hydrochloric acid when $P_1$ is formyl; or bi) reacting L-homocystine with ethyl trifluoroacetate to give the compound of the formula

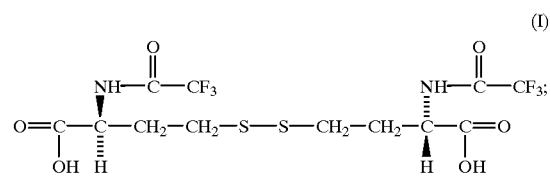
(I)

bii) converting the disulfide of formula I to the corresponding acid chloride by treating with (chloromethylene)dimethylammonium chloride;

biii) reacting the acid chloride from step (bii) with (S)-2-amino-6,6-dimethoxyhexanoic acid, methyl ester to give the compound of the formula

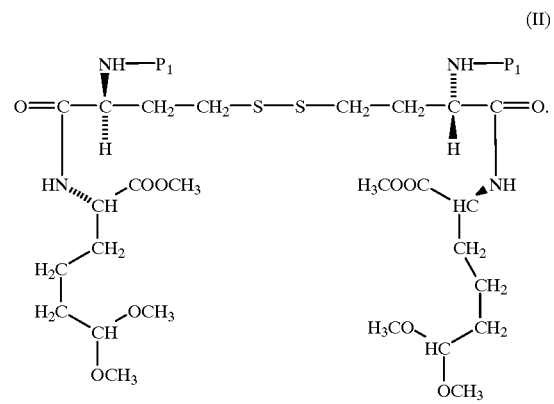
(II)

biv) reacting the disulfide of formula II with tributyl phosphine to cleave the disulfide bond;

bv) subjecting the monomer from step (biv) to an acid catalyzed cyclization reaction to give the N-protected lactam of the formula

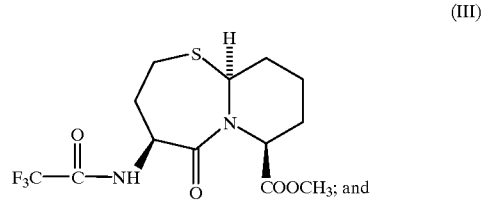
(III)

bvi) treating the N-protected lactam of formula III with potassium carbonate followed by hydrochloric acid; or ci) reacting L-homocystine with ethyl trifluoroacetate to give the compound of the formula

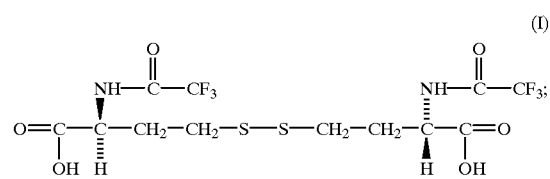
(I)

cii) reacting the disulfide of formula I with (S)-2-amino-6,6-dimethoxyhexanoic acid, methyl ester to give the disalt of the formula

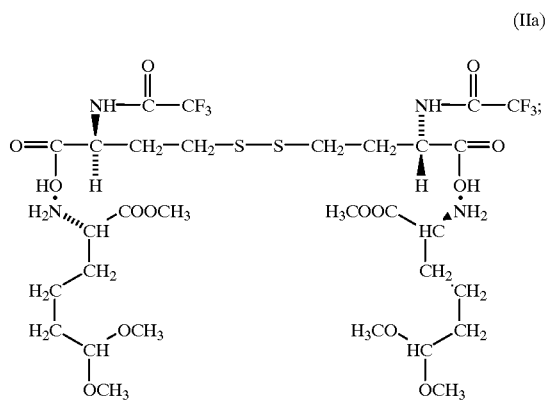

(IIa)

ciii) treating the compound of formula IIa with dicyclohexylcarbodiimide to give the disalt of the formula

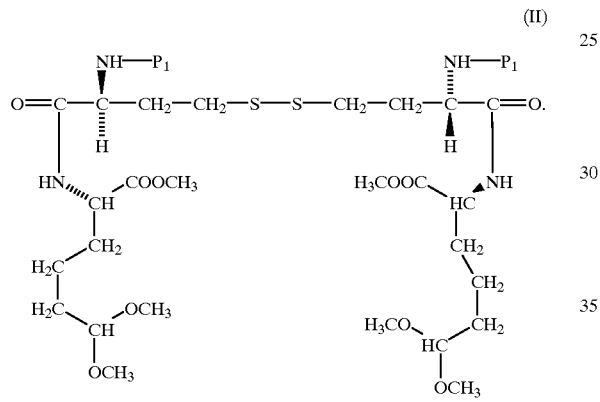

(II)

civ) reacting the disulfide of formula II with tributyl phosphine to cleave the disulfide bond;

cv) subjecting the monomer from part (civ) to an acid catalyzed cyclization reaction to give the N-protected lactam of the formula

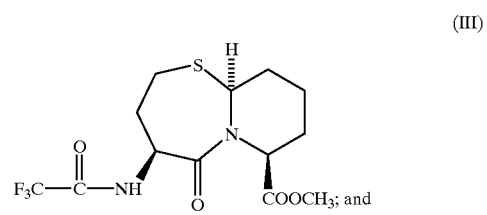

(III)

cvi) treating the N-protected lactam of the formula III with potassium carbonate followed by hydrochloric acid.

25. A process for preparing [4S-[4α(R*),7α,10aβ]]-octahydro-4-[(2-mercapto-1-oxo-3-phenylpropyl)amino]-5-oxo-7H-pyrido-[2,1-b][1,3]thiazepine-7-carboxylic acid which comprises:

a) reacting the disulfide of the formula

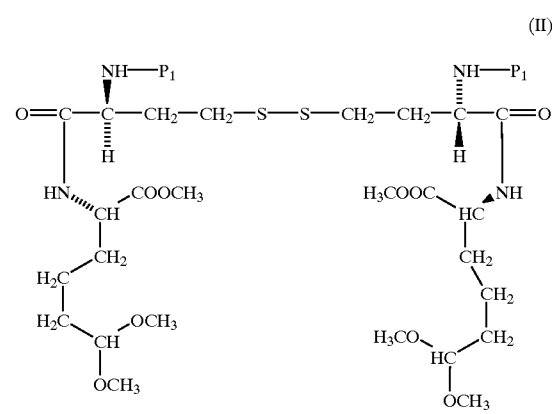

(II)

wherein $P_1$ is protecting group with a reagent that cleaves the disulfide bond;

b) subjecting the monomer from step (a) to an acid catalyzed cyclization reaction to give the N-protected lactam of the formula

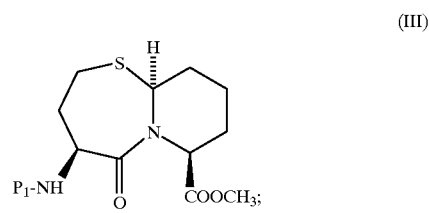

(III)

c) treating the N-protected lactam of formula III to remove the $P_1$ protecting group and give [4S-(4α,7α,10aβ)]-4-aminooctahydro-5-oxo-7H-pyrido[2,1-b][1,3]thiazepine-7-carboxylic acid, methyl ester;

d) coupling the lactam product from step (c) or a salt thereof with the acylmercaptoalkanoic acid of the formula

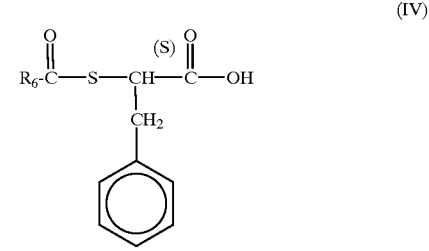

(IV)

wherein $R_6$ is methyl or phenyl to give the compound of the formula

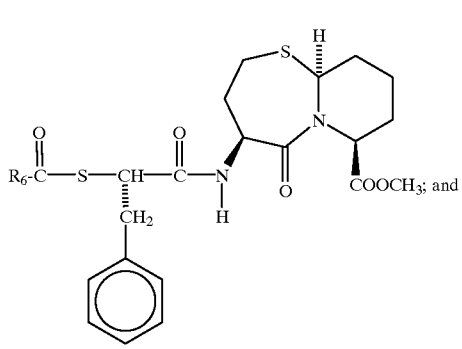
(V)

e) treating the compound of formula V to remove the R$_6$—C(O)— group and convert the methyl ester group to the carboxylic acid and yield the desired product.

26. A process for preparing [4S-[4α(R*),7α,10aβ]]-octahydro-4-[(2-mercapto-1-oxo-3-phenylpropyl)amino]-5-oxo-7H-pyrido-[2,1-b][1,3]thiazepine-7-carboxylic acid which comprises:

ai) reacting L-homocystine to introduce the group P$_1$ on both nitrogens and give the disulfide of the formula

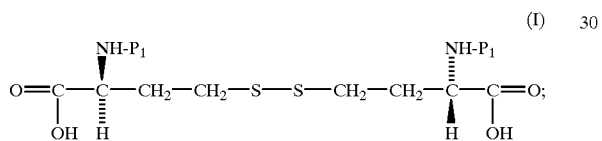
(I)

aii) reacting the disulfide of formula I with (S)-2-amino-6,6-dimethoxyhexanoic acid, methyl ester in the presence of a coupling reagent to give the disulfide of the formula

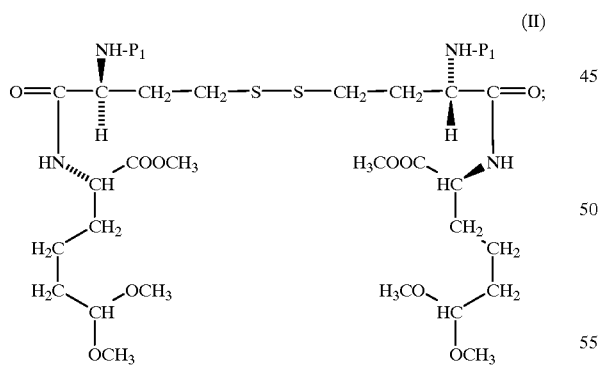
(II)

aiii) reacting the disulfide of formula II with a reagent that cleaves the disulfide bond;

aiv) subjecting the monomer from step (aiii) to an acid catalyzed cyclization reaction to give the N-protected lactam of the formula

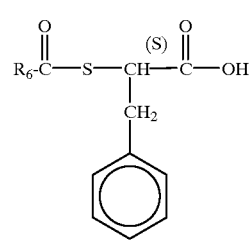
(III)

av) treating the N-protected lactam of formula III to remove the P$_1$ protecting group and give [4S-(4α,7α,10aβ)]-4-aminooctahydro-5-oxo-7H-pyrido[2,1-b][1,3]thiazepine- 7-carboxylic acid, methyl ester;

avi) coupling the lactam product from step (av) or a salt thereof with the acylmercaptoalkanoic acid of the formula

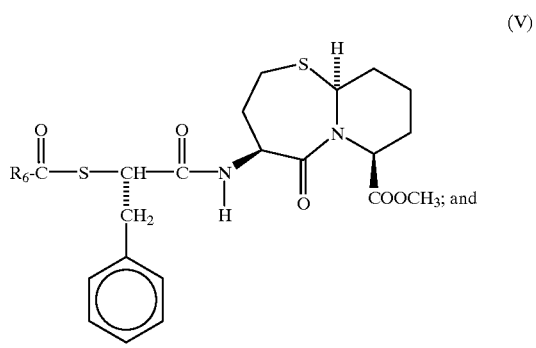
(IV)

wherein R$_6$ is methyl or phenyl to give the compound of the formula (V)

avii) treating the compound of formula V to remove the R$_6$—C(O)— group and convert the methyl ester group to the carboxylic acid and yield the desired product; or bi) reacting L-homocystine to introduce the group P$_1$ on both nitrogens and give the disulfide of the formula

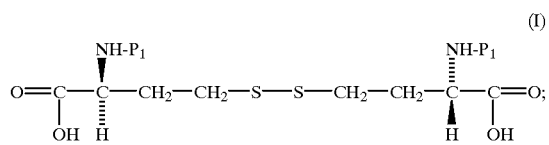
(I)

bii) converting the disulfide of formula I to an activated form;

biii) reacting the activated disulfide from step (bii) with (S)-2-amino-6,6-dimethoxyhexanoic acid, methyl ester to give the disulfide of the formula

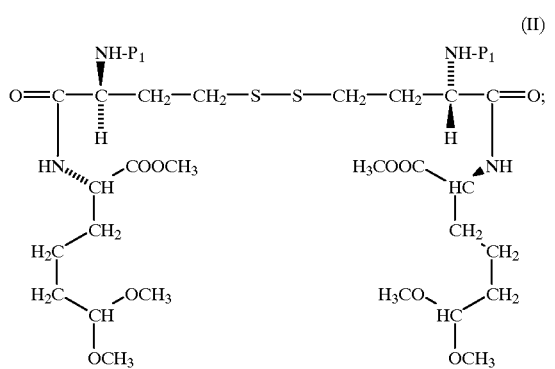

biv) reacting the disulfide of formula II with a reagent that cleaves the disulfide bond;

bv) subjecting the monomer from step (biv) to an acid catalyzed cyclization reaction to give the N-protected lactam of the formula

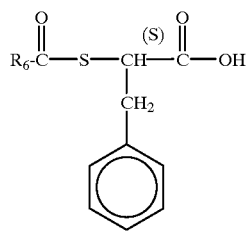

bvi) treating the N-protected lactam of formula III to remove the $P_1$ protecting group and give [4S-(4α,7α,10aβ)]-4-aminooctahydro-5-oxo-7H-pyrido[2,1-b][1,3]thiazepine-7-carboxylic acid, methyl ester;

bvii) coupling the lactam product from step (bvi) or a salt thereof with the acylmercaptoalkanoic acid of the formula

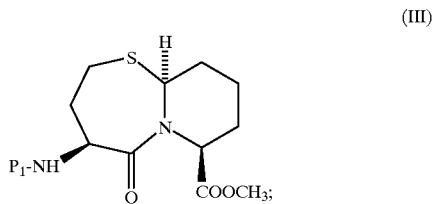

wherein $R_6$ is methyl or phenyl to give the compound of the formula

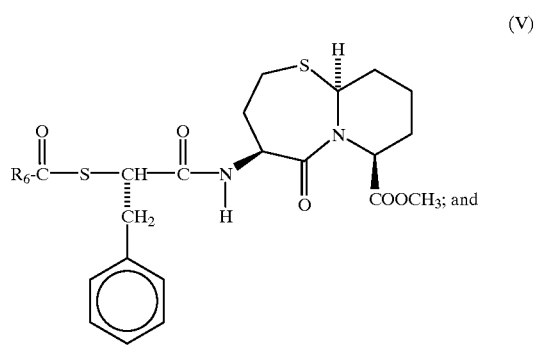

bviii) treating the compound of formula V to remove the $R_6$—C(O)— group and convert the methyl ester group to the carboxylic acid and yield the desired product; or ci) reacting L-homocystine to introduce the group $P_1$ on both nitrogens and give the disulfide of the formula

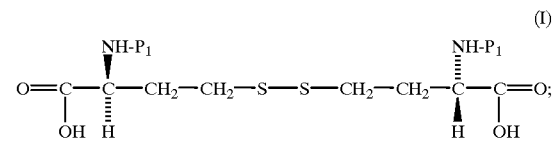

cii) reacting the disulfide of formula I with (S)-2-amino-6,6-dimethoxyhexanoic acid, methyl ester to give the disalt of the formula

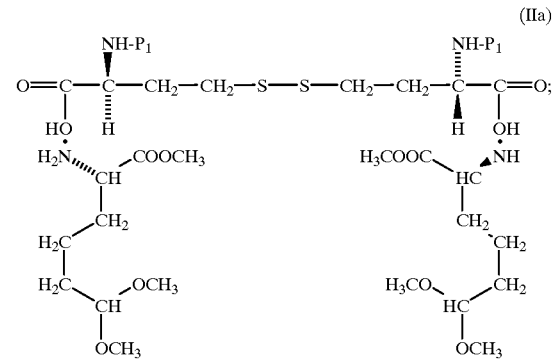

ciii) treating the compound of formula IIa with a coupling reagent to give the disulfide of the formula (II)

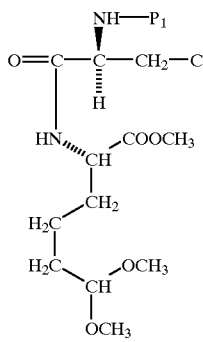
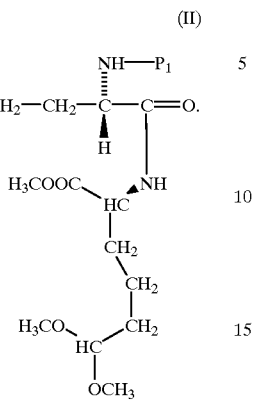

civ) reacting the disulfide of formula II with a reagent that cleaves the disulfide bond;

cv) subjecting the monomer from step (civ) to an acid catalyzed cyclization reaction to give the N-protected lactam of the formula (III)

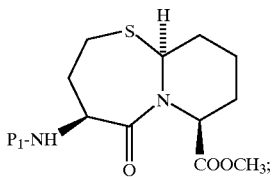

cvi) treating the N-protected lactam of formula III to remove the $P_1$ protecting group and give [4S-(4α,7α,10aβ)]-4-aminooctahydro-5-oxo-7H-pyrido[2,1-b][1,3]thiazepine-7-carboxylic acid, methyl ester;

cvii) coupling the lactam product from step (cvi) or a salt thereof with the acylmercaptoalkanoic acid of the formula (IV)

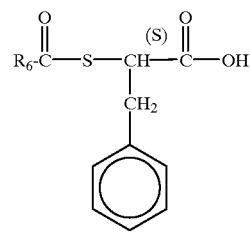

wherein $R_6$ is methyl or phenyl to give the compound of the formula (V)

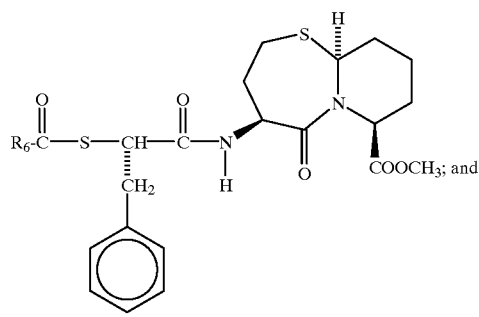

cviii) treating the compound of formula V to remove the $R_6$—C(O)— group and convert the methyl ester group to the carboxylic acid and yield the desired product.

27. The process of claim 9 wherein:
the disulfide of formula I or the activated form of the disulfide of formula I and (S)-2-amino-6,6-dimethoxyhexanoic acid, methyl ester are reacted in ethyl acetate and wherein the ethyl acetate solution of (S)-2-amino-6,6-dimethoxyhexanoic acid, methyl ester is first treated with an agent to remove ethylene glycol.

28. The process of claim 27 wherein:
the agent used to remove ethylene glycol is poly(acrylic acid-co-acrylamide), potassium salt or calcium chloride dihydrate.

* * * * *